(12) United States Patent
Fischer et al.

(10) Patent No.: US 8,721,332 B2
(45) Date of Patent: *May 13, 2014

(54) NON-CUSTOM DENTAL TREATMENT TRAYS HAVING IMPROVED ANATOMICAL FEATURES

(71) Applicant: Ultradent Products, Inc., South Jordan, UT (US)

(72) Inventors: Dan E. Fischer, Sandy, UT (US); Peter M. Allred, Bluffdale, UT (US); Neil T. Jessop, Sandy, UT (US); Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/742,080

(22) Filed: Jan. 15, 2013

(65) Prior Publication Data

US 2013/0130194 A1 May 23, 2013

Related U.S. Application Data

(62) Division of application No. 13/220,346, filed on Aug. 29, 2011, now Pat. No. 8,444,413, which is a division of application No. 11/836,664, filed on Aug. 9, 2007, now Pat. No. 8,007,277.

(60) Provisional application No. 60/932,982, filed on Aug. 25, 2006.

(51) Int. Cl.
*A61C 3/00* (2006.01)
*A61C 9/00* (2006.01)
*A61C 5/00* (2006.01)

(52) U.S. Cl.
USPC ............... 433/80; 433/215; 433/6; 433/37

(58) Field of Classification Search
USPC ............ 433/6, 24, 80, 215, 216, 34, 37; 128/859–861; 424/53
See application file for complete search history.

(56) References Cited

U.S. PATENT DOCUMENTS

| 165,584 A | 7/1875 | Hopfen |
| 1,637,153 A | 7/1927 | Lawton |

(Continued)

FOREIGN PATENT DOCUMENTS

| DE | 004011204 | 10/1990 |
| EP | 1438953 | 7/2004 |

(Continued)

OTHER PUBLICATIONS

U.S. Appl. No. 60/932,982, filed Aug. 25, 2006, McLean et al.

(Continued)

*Primary Examiner* — Yogesh Patel
(74) *Attorney, Agent, or Firm* — Workman Nydegger

(57) ABSTRACT

A non-custom, dental tray device includes a moisture-resistant barrier layer having a labial-buccal wall, a lingual wall, and a bottom wall. The dental tray device includes at least one of the following structural features to enhance the fit of the device; (1) the bottom wall includes an abrupt reduction of width at a location corresponding to where the first bicuspid meets the canine; (2) a bottom wall in the posterior region having a width that is equal to or less than the width of the bottom wall in the anterior region, with no lingual wall in the posterior region; or (3) a transition portion between the bottom wall and either the labial-buccal wall or the lingual wall has a larger radius of curvature as compared to a radius of curvature at a transition portion between the bottom wall the other of the labial-buccal wall and the lingual wall.

20 Claims, 11 Drawing Sheets

(56) References Cited

U.S. PATENT DOCUMENTS

| | | | |
|---|---|---|---|
| 1,663,695 A | 3/1928 | Forster, Jr. |
| 2,257,709 A | 9/1941 | Anderson |
| 2,835,628 A | 5/1958 | Saffir |
| 3,224,441 A | 12/1965 | Monaghan |
| 3,247,844 A | 4/1966 | Berghash |
| 3,312,218 A | 4/1967 | Jacobs |
| 3,319,626 A | 5/1967 | Lindsay |
| 3,339,547 A | 9/1967 | Drabkowski |
| 3,505,995 A | 4/1970 | Greenberg |
| 3,527,219 A | 9/1970 | Greenberg |
| 3,577,640 A | 5/1971 | Lee |
| 3,624,909 A | 12/1971 | Greenberg |
| 3,625,215 A | 12/1971 | Quisling |
| 3,688,406 A | 9/1972 | Porter et al. |
| 3,838,513 A | 10/1974 | Katz et al. |
| 3,878,610 A | 4/1975 | Coscina |
| 3,955,281 A | 5/1976 | Weitzman |
| 4,033,774 A | 7/1977 | Johnson et al. |
| 4,044,762 A | 8/1977 | Jacobs |
| 4,063,552 A | 12/1977 | Going et al. |
| 4,064,628 A | 12/1977 | Weitzman |
| 4,082,693 A | 4/1978 | Kessler et al. |
| 4,138,814 A | 2/1979 | Weitzman |
| 4,173,505 A | 11/1979 | Jacobs |
| 4,361,528 A | 11/1982 | Ginsburg et al. |
| 4,370,133 A | 1/1983 | Stempel |
| 4,401,616 A | 8/1983 | Wagner |
| 4,413,979 A | 11/1983 | Ginsburg et al. |
| 4,569,342 A | 2/1986 | Von Nostitz |
| 4,619,610 A | 10/1986 | Pelerin |
| 4,668,188 A | 5/1987 | Wolfenson et al. |
| 4,672,081 A | 6/1987 | Fischer et al. |
| 4,776,792 A | 10/1988 | Wagner et al. |
| 4,867,680 A | 9/1989 | Hare et al. |
| RE33,093 E | 10/1989 | Schiraldi et al. |
| 4,900,721 A | 2/1990 | Bansemir et al. |
| 4,902,227 A | 2/1990 | Smith |
| 5,008,093 A | 4/1991 | Merianos |
| 5,051,476 A | 9/1991 | Uji et al. |
| 5,066,231 A | 11/1991 | Oxman et al. |
| 5,085,585 A | 2/1992 | Zimble |
| 5,108,742 A | 4/1992 | Merianos |
| 5,112,225 A | 5/1992 | Diesso |
| 5,183,901 A | 2/1993 | Login et al. |
| 5,211,559 A | 5/1993 | Hart et al. |
| 5,213,498 A | 5/1993 | Pelerin |
| 5,277,202 A | 1/1994 | Hays |
| 5,277,203 A * | 1/1994 | Hays ............... 128/861 |
| 5,310,563 A | 5/1994 | Curtis et al. |
| 5,326,262 A | 7/1994 | Jorgenson |
| 5,326,685 A | 7/1994 | Gaglio et al. |
| 5,346,061 A | 9/1994 | Newman et al. |
| 5,356,291 A | 10/1994 | Darnell |
| 5,376,006 A | 12/1994 | Fischer |
| 5,409,631 A | 4/1995 | Fischer |
| 5,415,544 A | 5/1995 | Oxman et al. |
| 5,425,953 A | 6/1995 | Sintov et al. |
| 5,460,527 A | 10/1995 | Kittelsen |
| 5,462,067 A | 10/1995 | Shapiro |
| 5,503,552 A | 4/1996 | Diesso |
| 5,548,848 A | 8/1996 | Huybrechts |
| 5,562,449 A | 10/1996 | Jacobs et al. |
| 5,573,399 A | 11/1996 | McClintock, II |
| 5,575,654 A | 11/1996 | Fontenot |
| 5,582,517 A | 12/1996 | Adell |
| 5,591,786 A | 1/1997 | Oxman et al. |
| 5,611,687 A | 3/1997 | Wagner |
| 5,616,027 A | 4/1997 | Jacobs et al. |
| 5,631,000 A | 5/1997 | Pellico et al. |
| 5,639,445 A | 6/1997 | Curtis et al. |
| 5,702,251 A | 12/1997 | McClintock, II |
| 5,707,235 A | 1/1998 | Knutson |
| 5,711,935 A | 1/1998 | Hill et al. |
| 5,752,826 A | 5/1998 | Andreiko |
| 5,769,633 A | 6/1998 | Jacobs et al. |
| 5,770,182 A | 6/1998 | Fischer |
| 5,794,627 A | 8/1998 | Frantz et al. |
| 5,807,100 A | 9/1998 | Thornton |
| 5,816,802 A | 10/1998 | Montegomery |
| 5,829,441 A | 11/1998 | Kidd et al. |
| 5,846,058 A | 12/1998 | Fischer |
| 5,846,082 A | 12/1998 | Thornton |
| 5,851,512 A | 12/1998 | Fischer |
| 5,855,870 A | 1/1999 | Fischer |
| 5,863,202 A | 1/1999 | Fontenot et al. |
| 5,879,691 A | 3/1999 | Sagel et al. |
| 5,890,894 A | 4/1999 | Mio et al. |
| 5,891,453 A | 4/1999 | Sagel et al. |
| 5,894,017 A | 4/1999 | Sagel et al. |
| 5,895,218 A | 4/1999 | Quinn et al. |
| 5,922,307 A | 7/1999 | Montgomery |
| 5,924,863 A | 7/1999 | Jacobs et al. |
| 5,980,249 A | 11/1999 | Fontenot |
| 5,985,249 A | 11/1999 | Fischer |
| 5,989,569 A | 11/1999 | Dirksing et al. |
| 5,993,208 A | 11/1999 | Jonjic |
| 6,012,919 A | 1/2000 | Cross, III et al. |
| 6,017,217 A | 1/2000 | Wittrock |
| 6,036,943 A | 3/2000 | Fischer |
| 6,045,811 A | 4/2000 | Dirksing et al. |
| 6,080,397 A | 6/2000 | Pfirrmann |
| 6,089,869 A | 7/2000 | Schwartz |
| 6,096,328 A | 8/2000 | Sagel et al. |
| 6,106,293 A | 8/2000 | Wiesel |
| 6,126,443 A | 10/2000 | Burgio |
| 6,136,297 A | 10/2000 | Sagel et al. |
| 6,142,780 A | 11/2000 | Burgio |
| 6,155,832 A | 12/2000 | Wiesel |
| 6,183,251 B1 | 2/2001 | Fischer |
| 6,196,840 B1 | 3/2001 | Zentz et al. |
| 6,197,331 B1 | 3/2001 | Lerner et al. |
| 6,244,864 B1 | 6/2001 | Fujiwara et al. |
| 6,247,930 B1 | 6/2001 | Chiang et al. |
| 6,257,239 B1 | 7/2001 | Kittelsen et al. |
| 6,274,122 B1 | 8/2001 | McLaughlin |
| 6,277,458 B1 | 8/2001 | Dirksing et al. |
| 6,280,196 B1 | 8/2001 | Berghash |
| 6,287,120 B1 | 9/2001 | Wiesel |
| 6,309,625 B1 | 10/2001 | Jensen et al. |
| 6,312,671 B1 | 11/2001 | Jensen et al. |
| 6,314,960 B1 | 11/2001 | Vines |
| 6,322,360 B1 | 11/2001 | Burgio |
| 6,331,292 B1 | 12/2001 | Montgomery |
| 6,343,932 B1 | 2/2002 | Wiesel |
| 6,364,665 B1 | 4/2002 | Trettenero |
| 6,379,147 B1 | 4/2002 | Georgakis et al. |
| 6,398,550 B1 | 6/2002 | Caritg |
| 6,419,903 B1 | 7/2002 | Xu et al. |
| 6,419,906 B1 | 7/2002 | Xu et al. |
| 6,435,873 B1 | 8/2002 | Burgio |
| 6,440,396 B1 | 8/2002 | McLaughlin |
| 6,458,380 B1 | 10/2002 | Leaderman |
| 6,461,158 B1 | 10/2002 | Sagel et al. |
| 6,488,914 B2 | 12/2002 | Montgomery |
| 6,497,575 B2 | 12/2002 | Zavitsanos et al. |
| 6,500,408 B2 | 12/2002 | Chen |
| 6,503,486 B2 | 1/2003 | Xu et al. |
| 6,506,053 B2 | 1/2003 | Wiesel |
| 6,514,483 B2 | 2/2003 | Xu et al. |
| 6,514,484 B2 | 2/2003 | Rajaiah et al. |
| 6,551,579 B2 | 4/2003 | Sagel et al. |
| 6,649,147 B1 | 11/2003 | Ye et al. |
| 6,682,721 B2 | 1/2004 | Kim et al. |
| 6,689,344 B2 | 2/2004 | Chang et al. |
| 6,730,316 B2 | 5/2004 | Chen |
| 6,840,771 B1 | 1/2005 | Wagner |
| 6,860,736 B2 | 3/2005 | Allred et al. |
| 6,935,857 B1 | 8/2005 | Farrell |
| 6,964,571 B2 | 11/2005 | Andersen et al. |
| 7,040,897 B2 | 5/2006 | Fischer et al. |
| 7,052,275 B2 | 5/2006 | Allred et al. |
| 7,056,118 B2 | 6/2006 | Allred et al. |
| 7,059,857 B2 | 6/2006 | Allred et al. |
| 7,059,858 B2 | 6/2006 | McLean et al. |

(56) References Cited

U.S. PATENT DOCUMENTS

| | | |
|---|---|---|
| 7,137,814 B2 | 11/2006 | Fischer et al. |
| 8,007,277 B2 | 8/2011 | Fischer et al. |
| 8,444,413 B2 | 5/2013 | Fischer et al. |
| 2001/0046654 A1 | 11/2001 | Zavitsanos et al. |
| 2002/0006387 A1 | 1/2002 | Sagel et al. |
| 2002/0006388 A1 | 1/2002 | Sagel et al. |
| 2002/0012685 A1 | 1/2002 | Sagel et al. |
| 2002/0018754 A1 | 2/2002 | Sagel et al. |
| 2002/0081555 A1 | 6/2002 | Wiesel |
| 2002/0164292 A1 | 11/2002 | Peterson et al. |
| 2002/0182154 A1 | 12/2002 | McLaughlin |
| 2002/0187111 A1 | 12/2002 | Xu et al. |
| 2002/0187112 A1 | 12/2002 | Xu et al. |
| 2003/0003421 A1 | 1/2003 | Bestenheider et al. |
| 2003/0012747 A1 | 1/2003 | Peterson |
| 2003/0036037 A1 | 2/2003 | Zavitsanos et al. |
| 2003/0044631 A1 | 3/2003 | Sagel et al. |
| 2003/0068284 A1 | 4/2003 | Sagel et al. |
| 2003/0068601 A1 | 4/2003 | Zavitsanos et al. |
| 2003/0082114 A1 | 5/2003 | Kim et al. |
| 2003/0133884 A1 | 7/2003 | Chang et al. |
| 2003/0194382 A1 | 10/2003 | Chang et al. |
| 2003/0198606 A1 | 10/2003 | Kim et al. |
| 2004/0002035 A1 | 1/2004 | Jacobs et al. |
| 2004/0005277 A1 | 1/2004 | Willison et al. |
| 2004/0146837 A1 | 7/2004 | Andersen |
| 2004/0214140 A1 | 10/2004 | Fischer et al. |
| 2004/0234929 A1* | 11/2004 | Fischer et al. ............... 433/215 |
| 2004/0241620 A1* | 12/2004 | Allred et al. ............... 433/215 |
| 2005/0048443 A1 | 3/2005 | Jacobs et al. |
| 2005/0136381 A1 | 6/2005 | Andersen |
| 2005/0186539 A1 | 8/2005 | McLean et al. |
| 2006/0078848 A1 | 4/2006 | Fischer et al. |
| 2006/0084024 A1 | 4/2006 | Farrell |
| 2006/0219250 A1 | 10/2006 | Farrell |
| 2006/0223033 A1 | 10/2006 | McLean et al. |
| 2007/0298380 A1 | 12/2007 | Allred |
| 2008/0025925 A1 | 1/2008 | Allred |
| 2011/0311938 A1 | 12/2011 | Fischer et al. |

FOREIGN PATENT DOCUMENTS

| | | |
|---|---|---|
| JP | 406038988 | 2/1994 |
| WO | WO 88/06869 | 9/1988 |
| WO | WO 91/12777 | 9/1991 |
| WO | WO 93/08761 | 5/1993 |
| WO | WO 02/024100 | 3/2002 |
| WO | WO 03/000216 | 1/2003 |
| WO | WO 03/030851 | 4/2003 |
| WO | WO 2005/000147 | 1/2005 |

OTHER PUBLICATIONS

Technical Bulletin: Hydrogen Peroxide-Polyvinylpyrrolidone Polymer Complexes, International Specialty Products, 1361 Alps Rd. Wayne New Jersey 07470, www.ispcorp.com (Dec. 2003).
U.S. Appl. No. 10/423,242, Dec. 15, 2004, Office Action.
U.S. Appl. No. 10/423,242, May 19, 2005, Office Action.
U.S. Appl. No. 10/783,597, Apr. 5, 2005, Office Action.
U.S. Appl. No. 10/783,597, Dec. 9, 2005, Notice of Allowance.
U.S. Appl. No. 11/446,924, Dec. 30, 2008, Restriction Requirement.
U.S. Appl. No. 11/446,924, Mar. 30, 2009, Restriction Requirement.
U.S. Appl. No. 11/446,924, Dec. 10, 2009, Office Action.
U.S. Appl. No. 11/446,924, Jul. 2, 2010, Office Action.
U.S. Appl. No. 11/446,924, Sep. 21, 2010, Office Action.
U.S. Appl. No. 11/446,924, Jun. 8, 2011, Office Action.
U.S. Appl. No. 11/446,924, Nov. 21, 2001, Office Action.
U.S. Appl. No. 11/446,924, Feb. 23, 2012, Office Action.
U.S. Appl. No. 11/446,924, Jun. 14, 2012, Notice of Allowance.
U.S. Appl. No. 11/836,664, Jun. 3, 2009, Restriction Requirement.
U.S. Appl. No. 11/836,664, Sep. 25, 2009, Office Action.
U.S. Appl. No. 11/836,664, Mar. 10, 2010, Office Action.
U.S. Appl. No. 11/836,664, Sep. 13, 2010, Office Action.
U.S. Appl. No. 11/836,664, Dec. 27, 2010, Office Action.
U.S. Appl. No. 11/836,664, Apr. 28, 2011, Notice of Allowance.

* cited by examiner

NON-CUSTOM DENTAL TREATMENT TRAYS HAVING IMPROVED ANATOMICAL FEATURES

CROSS REFERENCE TO RELATED APPLICATIONS

The present application is a division of copending U.S. patent application Ser. No. 13/220,346, filed Aug. 29, 2011, which is a division of copending U.S. patent application Ser. No. 11/836,664, filed Aug. 9, 2007, which claims the benefit of provisional U.S. application Ser. No. 60/932,982, filed Aug. 25, 2006. The disclosures of the foregoing applications are incorporated herein in their entirety.

BACKGROUND OF THE INVENTION

1. The Field of the Invention

The present invention is in the field of dental tray shaped treatment devices used to provide a desired dental treatment to a person's teeth. The treatment device can be used for dental treatments such as bleaching, administration of fluoride, or application of other medicines.

2. The Relevant Technology

Virtually all people desire white or whiter teeth. A common bleaching method involves the use of a dental tray that is custom-fitted to a person's teeth and that is therefore comfortable to wear. One type of customized tray is made from a stone cast of a person's teeth. Another is customized directly using a person's teeth as a template (e.g., "boil-and-bite" trays). Non-customized trays that approximate the shapes and sizes of a variety of users' dental arches have also been used. A dental bleaching composition is placed into the tray and the tray placed over the person's teeth for a desired period of time.

Another tooth bleaching method involves placing a flexible bleaching strip over a user's tooth surfaces. Conventional bleaching strips comprise a flexible plastic strip coated with a dental bleaching gel of moderate viscosity and relatively low stickiness on the side of the strip facing the user's teeth. To install the bleaching strip, a portion of the bleaching strip is placed over the front surfaces of the user's teeth, and the remainder is folded around the occlusal edges of the teeth and against a portion of the lingual surfaces.

Because of the generally poor adhesion of bleaching strips to the user's teeth, coupled with their generally flimsy nature, it is often difficult for the user to maintain the bleaching strip in its proper position for the recommended time. Conventional bleaching strips are prone to slip off the teeth as a result of even minimal movement of the user's mouth, jaw or tongue. It is recommended that the user not eat, drink, smoke or sleep while wearing the bleaching strip. In some cases, the bleaching strip can become so dislodged or mangled that it must be removed by the user and replaced with a fresh bleaching strip to complete the recommended bleaching time.

Ultimately, the main impediment to successful bleaching is the failure of users to complete the prescribed bleaching regimen. If the bleaching apparatus is difficult to install over a person's teeth, requires numerous repetitions to achieve observable results, or is uncomfortable to wear, the user may simply give up and prematurely abort the prescribed bleaching regimen. Thus, even if dental bleaching is possible using a particular bleaching apparatus or method, it is less likely to occur if the inadequacies of the bleaching apparatus or method cause a user to become discouraged before desired results are attained.

In view of the foregoing, there is an ongoing need for improved bleaching apparatus and methods that are simple and easy to use and that reliably remain in position over the user's teeth so as to reduce diffusion of bleaching composition into a user's oral cavity. Such improvements would be expected to improve or encourage compliance by the user.

BRIEF SUMMARY OF THE PREFERRED EMBODIMENTS

The present invention is directed to non-custom dental tray devices suitable for placement over at least a portion of a person's dental arch. The dental tray device may comprise a dental treatment tray or mouth guard. The dental tray devices comprise a moisture-resistant barrier layer formed of a polymeric material having generally a horseshoe shape tray-like configuration that substantially corresponds to the curvature of a person's dental arch. The dental tray device includes a labial-buccal wall, a lingual wall, and a bottom wall interposed between the labial-buccal wall and the lingual wall. The dental tray device is non-customized (i.e., is substantially devoid of structures corresponding to the size and shape of a person's unique dentition so that the tray is designed to fit over a plurality of differently-sized and/or shaped teeth corresponding to different people).

The barrier layer includes one or more structural features that facilitate the ability of the barrier layer to better conform to a plurality of differently sized and/or shaped teeth when worn. The structural features included in the barrier layer include at least one of: (1) an abrupt reduction of a width of the bottom wall at a location corresponding to a transition between posterior teeth and anterior teeth to account for the significant difference between the occlusal surface width of the posterior teeth as compared to the anterior teeth; (2) a width of the bottom wall in the posterior region of the tray being equal to or less than a width of the bottom wall in the anterior region of the tray, and the lingual wall terminating at or before the transition between the posterior and anterior regions; (3) in a barrier layer configured for placement over an upper dental arch, a transition portion between the bottom wall and the lingual wall of the barrier layer having a radius of curvature that is larger as compared to a radius of curvature at a transition portion between the bottom wall and the labial-buccal wall; or (4) in a barrier layer that is configured for placed over a lower dental arch, a transition portion between the bottom wall and the labial-buccal wall having a radius of curvature that is larger as compared to a radius of curvature at a transition portion between the bottom wall and the lingual wall.

Non-custom dental tray devices including one or more of these structural features are better able to conform to the standard and natural contour of the teeth and/or gum tissue surrounding the dental arches. This is advantageous as it reduces the presence of gaps between the barrier layer and the tooth and/or gum tissue, which gaps can allow introduction of saliva and/or result in a looser fit of the tray over the dental arch, all of which act to reduce the effectiveness of a dental treatment in the case of a dental treatment tray. In the case of a mouth guard, these gap characteristics result in a fit which does not rest as close to the tooth and gum tissue as it otherwise could, which can result in a loose fit to such a mouth guard. In a worst case, such a mouth guard might be sufficiently loose so as to fall off, resulting in damage to the teeth while participating in a sport.

In the case of a dental treatment tray, the barrier layer is advantageously thin and flexible so that it can readily conform to a plurality of differently sized dental arches corresponding to different people. Generally, barrier layers for devices configured as dental treatment trays will have a thickness less than about 2 mm, more typically less than about 1 mm, and most preferably less than about 0.5 mm. For example, according to one particularly preferred embodiment the barrier layer has a thickness between about 0.1 and about 0.5 mm.

Mouth guards for use in sports are thicker so as to provide a cushioning effect to the teeth and surrounding gum tissue. An exemplary mouth guard may have a thickness greater than about 2 mm. Advantageously, it has been found that incorporation of one or more of the above described structural features allows the barrier layer of a mouth guard to be somewhat thinner for increased comfort while still providing the same level of protection, cushioning, and comfort as compared to a mouth guard that does not include any of the above structural features.

A related kit advantageously includes a first dental tray device as described above configured for placement over at least a portion of a person's lower dental arch and a second dental tray device configured for placement over at least a portion of a person's upper dental arch. Each dental tray device includes at least one of the described structural features. For example, the dental tray device configured for placement over a lower dental arch may include a bottom wall where a transition portion between the bottom wall and a labial-buccal wall has a radius of curvature that is larger as compared to a radius of curvature of a transition portion between the bottom wall and a lingual wall. Likewise, the second dental tray device that is configured for placement over an upper dental arch may advantageously include a transition portion between a bottom wall and a lingual wall that has a radius of curvature that is larger as compared to a radius of curvature of a transition portion between the bottom wall and a labial-buccal wall.

The dental trays may further advantageously include an abrupt narrowing of the width of the bottom wall at a location corresponding to a transition portion between posterior teeth and anterior teeth (i.e., between the first bicuspids and the canines), to account for the significant difference between the occlusal surface width of the posterior teeth as compared to the anterior teeth. Alternatively, one or both dental trays may include a bottom wall which has a width in the posterior region (i.e., posterior to the first bicuspid-canine transition) of the tray that is equal to or less than a width of the bottom wall in the anterior region of the tray, and in which the lingual wall terminates at or before the transition between the posterior and anterior regions.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction and Definitions

Figure 1A:
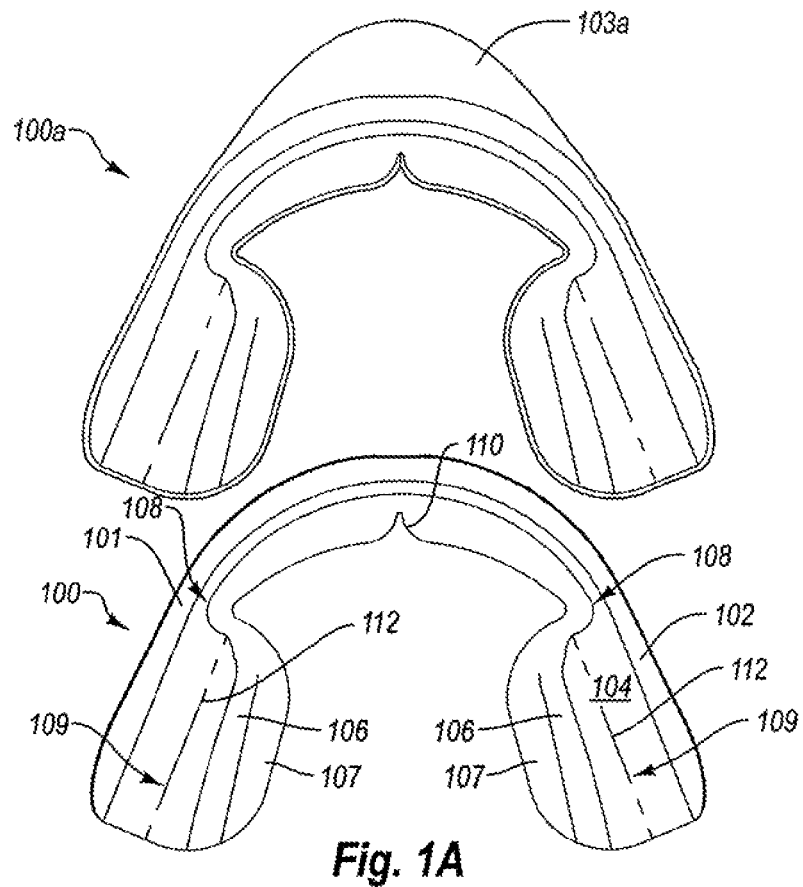
FIG. 1A is a perspective view of an exemplary dental treatment tray configured to fit over at least a portion of a person's upper dental arch, next to an associated exoskeleton.

The inventive non-custom tray-shaped dental tray devices include a moisture-resistant barrier layer having a labial-buccal wall, a lingual wall, and a bottom wall interposed therebetween. In addition, the tray-shaped dental treatment device includes at least one of the following structural features to enhance the fit of the device over a plurality of differently-sized and/or shaped teeth without requiring any customization: (1) the bottom wall including an abrupt reduction of its width positioned to help the bottom wall better conform to abrupt changes in the occlusal surface width of a person's posterior teeth versus anterior teeth; (2) a width of the bottom wall in the posterior region of the tray being equal to or less than a width of the bottom wall in the anterior region of the tray, and the lingual wall terminating at or before the transition between the posterior and anterior regions; (3) in a device configured for placement over a lower dental arch, a transition portion between the bottom wall and the labial-buccal wall having a larger radius of curvature as compared to a radius of curvature at a transition portion between the bottom wall and the lingual wall; or (4) in a device configured for placement over an upper dental arch, a transition portion between the bottom wall and the lingual wall having a larger radius of curvature as compared to a radius of curvature at a transition portion between the bottom wall and the labial-buccal wall.

The tray devices may comprise a dental treatment tray (e.g., used for tooth bleaching or other treatment) or a mouth guard (e.g., used to protect the dental arches while participating in a contact sport). Generally, dental treatment tray devices are characterized as being relatively thin (e.g., less than about 2 mm), while mouth guards are thicker (e.g., greater than about 2 mm).

In the context of a dental treatment tray (e.g., as used for tooth bleaching), the term "barrier layer", refers to one or more layers of a moisture-resistant material that protects a treatment composition and/or adhesive composition layer from ambient moisture and saliva found within a person's mouth when the dental treatment tray is placed over the person's teeth. The barrier layer may also serve to protect a treatment composition and/or adhesive composition from moisture or other contaminants during storage and prior to use.

In the context of a mouth guard, the barrier layer is thicker than a barrier layer of a dental treatment tray used for tooth and/or gum treatment (e.g., greater than about 2 mm for a mouth guard versus less than about 2 mm, less than about 1 mm, and most preferably between about 0.5 and about 0.25 mm for a dental treatment tray). The barrier layer of a mouth guard serves to protect the hard and soft tissue (e.g., the teeth and gums) while participating in a sport or other activity in which a blow to the jaw or face might otherwise damage the person's teeth. Because the barrier layer includes one or more structural features to enhance fit, the non-custom barrier layer is better able to cradle, support, and protect hard and soft tissues as compared to a non-custom barrier layer mouth guard device that does not include such features. Furthermore, because of the enhanced fit, the barrier layer can be thinner relative to a mouth guard barrier layer without the structural features, while still providing the same level of protection. The relatively thin mouth guard barrier layer is advantageously more comfortable than a thicker mouth guard barrier layer.

The term "gel" refers to treatment and/or adhesive compositions that have been formulated or processed so as to be flowable, either by the force of gravity (i.e., having no yield stress) or that do not flow by the force of gravity but which are viscous or plastic such that they can be shaped or manipulated (e.g., they can be expressed from a syringe orifice or other dispensing means known in the art). The term "gel" broadly encompasses a wide range of compositions having greatly varying viscosities, although treatment and adhesive gels used with the inventive devices are preferably sufficiently thick or viscous that they will not run out of or off of a barrier layer by gravity alone. In one embodiment, the treatment and/or adhesive gel may be rubbery or highly viscous. At some point, when the viscosity becomes so great as to yield a composition that is substantially solid (e.g., a stiff or highly viscous putty), the composition may be considered to be "substantially solid".

The term "substantially solid," as used herein, refers to a composition (e.g., a treatment composition) that is in a solid or semi-solid condition. One characteristic of "substantially solid" adhesive compositions used with the inventive dental treatment devices is that they become more adhesive when an exposed surface thereof is moistened with, e.g., saliva or water. When moistened, the surface of the adhesive composition turns into a sticky material that is able to more strongly adhere to teeth compared to a substantially solid adhesive composition that has not been moistened. The composition at the surface may become a viscous liquid, paste or gel, at least temporarily, depending on the amount of moisture that is applied to the surface of the "substantially solid" adhesive composition. Nevertheless, the consistency of the moistened surface can remain "substantially solid" depending on the degree of initial moistening, or it can stiffen and even revert back to being "substantially solid" as the initial quantity of surface moisture diffuses into a remaining portion of the "substantially solid" adhesive composition over time (e.g., during a bleaching procedure in which the composition is protected from saliva and ambient moisture in a person's mouth by a moisture-resistant barrier layer).

The term "molecular weight", as used herein, refers to number average molecular weight expressed in Daltons unless otherwise specified.

II. Exemplary Pre-Shaped Non-Custom Dental Tray Devices

A. Barrier Layer

The pre-shaped, non-custom dental tray devices include a barrier layer. According to one embodiment of the invention (e.g., a dental treatment tray used for tooth bleaching and/or other treatments), the barrier layer comprises a thin (e.g., about 2 mm or less), flexible membrane formed from a moisture-resistant polymer material. In another embodiment (e.g., a sport mouth guard), the barrier layer comprises a thicker (e.g., about 2 mm or more) flexible membrane formed from a moisture-resistant polymer material. In a preferred embodiment, the barrier layer comprises a mixture of ethyl vinyl acetate and polypropylene.

According to another embodiment, it may be formed of a polyolefin or similarly moisture-resistant material, such as wax, metal foil, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes or polyesteramides. Examples of suitable polyolefins for use in making the barrier layer include, but are not limited to, polyethylene (PE), high density polyethylene (HDPE), low density polyethylene (LDPE), ultra low density polyethylene (ULDPE), polypropylene, and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. An example of a suitable polyurethane barrier material is a polyurethane film manufactured by ArgoTech, which is located in Greenfield, Mass. The barrier layer may comprise a polymeric blend and/or multiple layers comprising two or more of the foregoing materials. Plasticizers, flow additives, and fillers known in the art can be used as desired to modify the properties of any of the foregoing polymers used to form the barrier layer.

According to one embodiment, the barrier layer is formed of a mixture of ethylene-vinyl acetate copolymer (EVA) and polypropylene (PP), preferably comprising about 5% to about 35% PP, more preferably about 10% to about 30% PP, more especially preferably about 15% to about 25% PP, and most preferably about 20% PP, with the balance comprising ethylene-vinyl acetate (EVA), and optionally other polymers and/or small quantities of additives such as plasticizers.

Other materials that can act as a barrier layer include cellulosic ethers, cellulose acetate, polyvinyl acetate, polyvinyl alcohol, shellac, and chemical or light-cure materials (e.g., methacrylate or acrylate resins). Examples of useful cellulosic ethers that can be used to form a barrier layer include, but are not limited to, ethyl cellulose, propyl cellulose, isopropyl cellulose, butyl cellulose, t-butyl cellulose, and the like.

In general, the thickness of the barrier layer can be selected to yield a dental treatment tray or mouth guard having a desired level of strength, rigidity, resilience, and flexibility. In the case of a dental treatment tray, it is desirable for the barrier layer to be sufficiently flexible so as to conform to a person's teeth as a result of adhesive action by the treatment composition and/or adhesive composition. As such, the barrier layer will preferably have a thickness ranging from about 0.025 mm to about 2 mm, more preferably in a range of about 0.05 mm to about 1 mm, and most preferably in a range of about 0.1 mm to about 0.5 mm.

In the case of a sport mouth guard, the balance between a desired degree of flexibility and comfort versus strength, resilience, and cushioning ability result in a barrier layer that is relatively thicker, preferably having a thickness ranging from about 2 mm to about 5 mm, more preferably from about 2 mm to about 4 mm, and most preferably from about 2 mm to about 3 mm. Because the barrier layer includes one or more structural features to enhance fit, less thickness is required for any given level of protection and cushioning ability relative to a mouth guard that does not include any of the structural features. This allows for use of a thinner mouth guard, which is also more comfortable to wear for the user.

B. Dental Treatment Compositions

In the case of a dental treatment tray used for whitening or otherwise treating a person's teeth and/or gums, a dental treatment composition may be applied adjacent one or more of the walls of the tray device. The treatment compositions may comprise any dental treatment composition known in the art. The treatment composition may comprise a sticky viscous gel, a less viscous gel, a highly viscous putty, or a substantially solid adhesive composition that is less adhesive prior to being moistened with saliva or water but that becomes more sticky and adhesive when moistened. The treatment compositions may comprise a continuous layer or bead positioned so as to cover a person's front tooth surfaces, rear tooth surfaces, or both, or they may comprise separate beads, layers or islands separated by one or more spaces. The treatment composition is advantageously positioned directly adjacent to the barrier layer.

In general, dental treatment gels will include at least one dental treatment agent, at least one tissue adhesion (or thickening) agent, and a liquid or gel, solvent, carrier, or vehicle into which the dental treatment agent and tissue adhesion agent are dispersed. The treatment gel may optionally include other active agents (e.g., desensitizing agents, remineralizing agents, antimicrobial agents, and the like), as well as inert ingredients (e.g., plasticizers, humectants, neutralizing agents, thickening agents, flavorants, sweeteners, and the like).

Exemplary dental treatment gels, and methods for making such gels, which may be used with devices according to the invention are disclosed in U.S. Pat. No. 5,376,006; U.S. Pat. No. 5,785,527; U.S. Pat. No. 5,851,512; U.S. Pat. No. 5,858,332; U.S. Pat. No. 5,985,249; U.S. Pat. No. 6,306,370; U.S. Pat. No. 6,309,625; U.S. Pat. No. 6,312,671; U.S. Pat. No. 6,322,774; U.S. Pat. No. 6,368,576; U.S. Pat. No. 6,387,353; U.S. Pat. No. 6,500,408; U.S. Pat. No. 6,503,485 and U.S. patent application Ser. No. 11/460,016 filed Jul. 26, 2006. For purposes of disclosing dental treatment gels, and methods of making such gels, the foregoing patents and application are incorporated herein by reference.

Following are preferred treatment agents, tissue adhesion agents, solvents or carriers, and other components within preferred treatment compositions that can be used within the inventive dental treatment devices.

1. Treatment Agents

Any treatment agent capable of treating teeth can be used. Examples include dental bleaching agents, desensitizing agents, antimicrobial agents, anticariogenic agents, and the like. A common dental bleaching agent that is known to bleach teeth and that has been found to be safe for oral use is hydrogen peroxide. However, stable hydrogen peroxide does not itself exist free in nature, but as an aqueous solution or a complex. Aqueous hydrogen peroxide is an acceptable dental treatment agent to the extent that an anhydrous treatment composition is not desired. Non-limiting examples of hydrogen peroxide complexes include carbamide peroxide and metal perborates (e.g., sodium perborate). Other bleaching agents that can be used to bleach teeth include, but are not limited to, metal percarbonates (e.g., sodium percarbonate), metal peroxides (e.g., calcium peroxide), metal chlorites and hypochlorites, peroxy acids (e.g., peroxyacetic acid), and peroxy acid salts.

The bleaching agent can have any desired concentration, e.g., between about 1-90% by weight of the treatment composition. The concentration of the dental bleaching agent can be adjusted depending on the intended treatment time for each treatment session. In general, the shorter the treatment time, the more bleaching agent will be added to accelerate dental bleaching so as to effect treatment in a shorter time period. The one or more bleaching agents are preferably included in an amount in a range of about 1% to about 60% by weight of the dental bleaching composition, more preferably in a range of about 5% to about 40% by weight, and most preferably in a range of about 10% to about 30% by weight.

The treatment composition may include one or more other active agents instead of, or in addition to, a bleaching agent to yield treatment compositions having desired properties. Examples of other active agents include, but are not limited to, desensitizing agents (e.g., potassium nitrate, other potassium salts, citric acid, citrates, and sodium fluoride), remineralizing agents (e.g., sodium fluoride, stannous fluoride, sodium monofluorophosphate, and other fluoride salts), antimicrobial agents (e.g., chlorhexidine, troclosan, and tetracycline), antiplaque agents, anti-tartar agents (e.g., pyrophosphates salts), and other medicaments. Such active agents may be included in amounts customary in the art of dental treatments.

2. Tissue Adhesion Agents

Useful tissue adhesion agents (or tackifying agents), which can also act as thickening agents that increase the viscosity of the dental treatment composition (e.g., a gel, a putty, or a substantially solid adhesive composition), include a wide variety of hydrophilic polymers. Examples of hydrophilic polymer tissue adhesion agents include, but are not limited to, polyvinyl pyrrolidone (PVP), PVP-vinyl acetate copolymers, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, carboxymethylcellulose, carboxypropylcellulose, cellulosic ethers, polysaccharide gums, proteins, and the like.

Non-limiting examples of polyvinyl pyrrolidone polymers that have been used in formulating dental treatment compositions include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million.

The treatment composition can be a gel, a putty, or substantially solid. The main difference between a composition that is a "gel" or "substantially solid" is the level of solvent or carrier within the composition. In general, the greater the concentration of solvent or carrier relative to the tissue adhesive agent, the less viscous the gel. The lower the concentration of solvent or carrier relative to the tissue adhesion agent, the more viscous the gel. At some point, the ratio of solvent or carrier to tissue adhesion agent is low enough so that the composition is or becomes a stiff or highly viscous putty, which may be characterized as being "substantially solid". Stiff putties preferably become more adhesive to teeth when moistened with water or saliva. Substantially solid adhesive compositions can have so little solvent or carrier as to feel dry to the touch and be initially non-adhesive but then become adhesive to teeth when moistened with water or saliva. Substantially solid adhesive compositions can be made by initially including a very small amount of solvent or carrier and/or by first forming an adhesive gel that is later dried to remove a substantial portion of the solvent or carrier.

Examples of substantially solid adhesive compositions that can be used to reliably maintain a barrier layer against a person's tooth surfaces are disclosed in U.S. Pat. No. 7,059,857; U.S. Pat. No. 7,056,118; and U.S. Pat. No. 7,052,275. For purposes of disclosing substantially solid adhesive compositions, the foregoing patents are incorporated herein by reference. Examples of adhesive gel compositions are disclosed in U.S. Pat. No. 5,770,182; U.S. Pat. No. 5,855,870; U.S. Pat. No. 5,851,512; U.S. Pat. No. 5,985,249; and U.S. Pat. No. 6,036,943. For purposes of disclosing adhesive gel compositions, the foregoing patents are incorporated herein by reference.

To form a gel having a desired rheology, the one or more tissue adhesion agents are preferably included in an amount in a range of about 1% to about 50% by weight of the dental treatment gel, more preferably in a range of about 3% to about 30% by weight, and most preferably in a range of about 5% to about 20% by weight. In the case where the treatment composition is substantially solid, the one or more tissue adhesion agents are preferably included in an amount in a range of about 10% to about 90% by weight of the substantially solid adhesive composition, more preferably in a range of about 20% to about 80% by weight, and most preferably in a range of about 40% to about 75% by weight.

In one embodiment, a dental treatment tray includes a layer or region of a substantially solid adhesive composition, and a treatment gel or putty adjacent to the barrier layer and/or the adhesive composition. The adhesive composition may be formulated to provide the same treatment as the separate gel or putty treatment composition, a different treatment, or no treatment. It may provide a protective barrier between the treatment agent in the gel or putty and the person's relatively sensitive gum tissue. It may include a bleaching agent activator in the case where the gel or putty includes a bleaching agent. Additional details regarding such configurations are disclosed in U.S. patent application Ser. No. 11/474,759 filed Jun. 26, 2006, herein incorporated by reference.

3. Carriers and Vehicles

Dental treatment gels for use with dental treatment trays according to the invention will typically include one or more liquid or gel solvents, carriers, or vehicles into which the dental treatment agent, tissue adhesion agent, and other components are dissolved or dispersed. The solvent, carrier, or vehicle will typically comprise the balance of components in the dental treatment gel in addition to the treatment agent, tissue adhesion agent, and other components.

Examples of liquid or gel solvents, carriers or vehicles include, but are not limited to, water, alcohols (e.g., ethyl alcohol), and polyols (e.g., glycerin, sorbitol, mannitol, other sugar alcohols, propylene glycol, 1,3-propanediol, polyethylene glycol, polyethylene oxide, and polypropylene glycol).

4. Other Components

The treatment compositions may optionally include other components as desired to yield treatment compositions having desired properties. Examples include bleaching agent stabilizers (e.g., EDTA, salts of EDTA, citric acid and its salts, phosphoric acid and its salts, phenolphosphonic acid and its salts, gluconic acid and its salts, alkali metal pyrophosphates, alkali metal pyrophosphates, alkyl sulfates, such as sodium lauryl sulfate, tin salts, such as sodium stannate, and tartrates), neutralizing agents (e.g., sodium hydroxide and triethanolamine), humectants, flavorants, sweeteners, inorganic rheology-modifying agents (e.g., fumed silica), and the like. Exemplary dental bleaching compositions including an inorganic rheology-modifying agent in addition to a generally linear high molecular weight (i.e., greater than about 500,000) polyvinyl pyrrolidone (PVP) and/or polyethylene oxide (PEO) tissue adhesion agent are disclosed in U.S. patent application Ser. No. 11/460,016 filed Jul. 26, 2006, herein incorporated by reference.

C. Characteristics of Pre-Shaped Non-Custom Dental Tray Devices

The pre-shaped, non-custom dental tray devices according to the invention are advantageously in the shape of a dental tray having a labial-buccal wall, a lingual wall, and a bottom wall interposed between the labial-buccal wall and the lingual wall. The three walls define an interior trough configured to receive at least a portion of a person's dental arch. The basic tray shape of the device facilitates placement of the device over a person's teeth by reducing the amount of manipulation necessary to obtain a good fit between the device and the person's teeth. The tray is non-custom. In other words, it is substantially devoid of structures corresponding to the size and shape of a person's unique dentition so that the tray devices are designed to comfortably fit over a plurality of differently-sized and/or shaped teeth corresponding to different people.

The pre-shaped non-custom dental tray devices include at least one, and preferably two of the following structural features to enhance the ability of the device to conform to the patient's teeth without customization: (1) the bottom wall includes an abrupt reduction of width positioned at a location corresponding to a transition between posterior and anterior teeth to account for a significant difference between the occlusal surface width of a person's posterior teeth as compared to the person's anterior teeth; (2) in a device configured for placement over a lower dental arch, a transition portion between the bottom wall and the labial-buccal wall has a larger radius of curvature as compared to a radius of curvature at a transition portion between the bottom wall and the lingual wall; and (3) in a device configured for placement over an upper dental arch, a transition portion between the bottom wall and the lingual wall has a larger radius of curvature as compared to a radius of curvature at a transition portion between the bottom wall and the labial-buccal wall.

FIG. 1A illustrates a perspective view of an exemplary pre-shaped, non-custom dental treatment tray 100, along with an associated exoskeleton 100a having a handle 103a. The treatment tray 100 of FIG. 1A is sized and configured for placement over a person's upper dental arch. Device 100 comprises a moisture resistant barrier layer 101 having a labial-buccal wall 102, a bottom wall 104, and a lingual wall 106.

The bottom wall 104 includes an abrupt reduction in width positioned at locations 108 corresponding to a transition between posterior teeth (i.e., bicuspids and molars) and anterior teeth (i.e., canines and incisors). Because there is a significant difference in occlusal surface width of the posterior teeth relative to the anterior teeth, particularly between the first bicuspid and the canine, an abrupt reduction in bottom wall width at a location of the barrier layer corresponding to the transition from the first bicuspid to the canine helps the bottom wall 104 and the lingual wall 106 to better conform to the teeth in this area. In other words, the sharp and abrupt reduction of width of the bottom wall 104 helps to compensate for the fact that bicuspids are significantly thicker than canines by allowing for an abrupt narrowing of the bottom wall 104 of the treatment device 100.

Without this narrowing of the bottom wall, it would be much more difficult to conform the bottom wall 104 to the canines since the adjacent bicuspids would tend to push the bottom wall 104 away from the canines, potentially dislodging the bottom wall 104 in this region. Because the bottom wall is continuous, rather than including one or more cuts at locations 108, little or no manipulation and forming of the barrier layer is required when fitting the treatment tray 100 over the dental arch. Advantageously, the treatment tray is simply aligned with the dental arch so that narrowing locations 108 of the bottom wall are inserted between the first bicuspids and the canines on each side of the dental arch (see FIGS. 7A-7B). In addition, it has been found that the use of cuts or discontinuities within bottom wall 104 at locations 108 may allow the patient's tongue to lodge between the dental arch and the barrier layer, lifting the tray off the dental arch. Because the bottom wall is continuous, there is reduced risk that the treatment and/or adhesive composition will be exposed to saliva or disruption from direct contact with the tongue during treatment, as could potentially occur if there were cuts or discontinuities within the bottom wall.

Bottom wall 104 has the greatest width across the portion intended to receive bicuspids and/or molars near region 109 which has a width between about 8 mm and about 12 mm (e.g., about 10 mm). At location 108 the width narrows abruptly (e.g., within a distance of about 3 mm or less) to a width between about 1 mm and about 3 mm (e.g., about 1.5 mm). Described another way, the width of bottom wall 104 is reduced between about 60 percent and about 95 percent, more preferably between about 75 percent and about 90 percent, and most preferably between about 80 percent and about 90 percent. These ranges have been found to provide a good fit for the majority of adult upper dental arches.

The posterior portion (e.g., near regions 109) of bottom wall 104 and lingual wall 106 includes a transition portion between bottom wall 104 and lingual wall 106 where the radius of curvature at the transition portion is greater than the radius of curvature at a transition portion between bottom wall 104 and labial-buccal wall 102. This difference in curvature on the lingual side versus the labial-buccal side of the tray accounts for the difference in angulation and orientation of the teeth, particularly the posterior teeth, on the lingual tooth surfaces versus the labial-buccal tooth surfaces. These curvature configurations allow the non-custom tray to better conform to the upper dental arch. Additional details of the configuration of the transition area between the bottom wall 104 and the lingual wall 106 as compared to the transition area between the bottom wall 104 and the labial-buccal wall 104 will be further described below in conjunction with FIG. 8A.

In addition, the posterior portion of lingual wall 106 may advantageously include an "S" type curve to advantageously provide a more comfortable fit against lingual gum tissue adjacent the posterior teeth of the upper dental arch. In other words, at a posterior portion, lingual wall 106 is configured to have a relatively steep angle (e.g., about 90° to about 110°) relative to bottom wall 104 immediately adjacent to a transition from bottom wall 104 to lingual wall 106, and part way up lingual wall 106 there is an inflection line or region, such that the extreme upper posterior portion 107 of lingual wall 106 is flared in a lingual direction so as to have a more open angle relative to bottom wall 104 (e.g., about 120° to about 140°) so as to fit more comfortably against the lingual gum tissue adjacent to the upper dental arch. The lingual gum tissue adjacent the upper dental arch (i.e., along the roof of the mouth) generally exhibits a relatively more gentle sloping surface as compared to the labial gum tissue, as well as the lingual gum tissue adjacent the lower dental arch, which is generally nearly parallel to the labial and lingual surfaces of the teeth. Such an "S" type curve is particularly helpful within a device configured for use over the upper dental arch, as it is only the lingual gum tissue adjacent the upper dental arch that exhibits such a gentle sloping surface. In other words, the lingual gum tissue adjacent the lower dental arch slopes away from the dental arch at a much steeper surface slope, such that an "S" type curve within lingual wall 106' (FIG. 1B) is not necessary, although it is within the scope of the invention to provide such a curve in lingual wall 106' of the lower dental treatment tray 100'.

As illustrated, the bottom wall may advantageously include a notch 110 near the front of bottom wall 104 of treatment tray 100. Optional notch 110 allows the non-custom dental treatment tray 100 to more easily spread open or compress in the area of the incisors. This is helpful in allowing the bottom wall 104 of the non-custom tray to more easily conform to differently-sized dental arches. As illustrated, notch 110 may have rounded exterior corners.

In the illustrated embodiment, the bottom wall 104 also advantageously includes two V-shaped indentations 112 configured to be inserted into the depression typically found along the top surfaces of a person's left and right posterior teeth (e.g., bicuspids and/or molars). Such a feature provides a dental tray device that better conforms to the person's teeth, resulting in a more comfortable fit, as further illustrated in FIGS. 8A-8B.

Figure 1B:
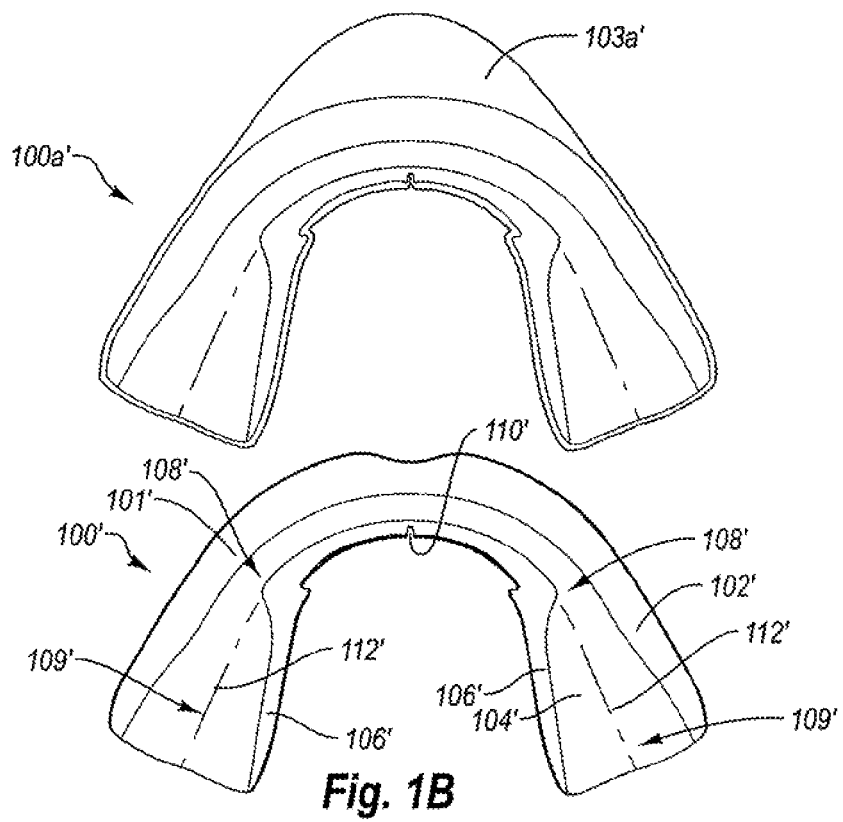
FIG. 1B is a perspective view of an exemplary dental treatment tray configured to fit over at least a portion of a person's lower dental arch, next to an associated exoskeleton.

FIG. 1B illustrates a perspective view of an exemplary dental treatment tray 100' along with an associated exoskeleton 100a' having a handle 103a'. The pre-shaped non-custom dental treatment tray 100' is sized and configured for placement over a person's lower dental arch. The non-custom dental treatment tray 100' includes a barrier layer 101' of moisture resistant material having a labial-buccal wall 102', a lingual wall 106', and a bottom wall 104'. Bottom wall 104' abruptly narrows in width at location 108', which corresponds to the transition from the posterior teeth (e.g., bicuspids and molars) to the anterior teeth (e.g., canines and incisors), which anterior teeth have a significantly smaller occlusal surface width and diameter as compared to the posterior teeth. Bottom wall 104' further includes an optional notch 110' and two V-shaped indentations 112'.

Bottom wall 104' preferably has its greatest width across the portion intended to receive bicuspids and/or molars near region 109', which has a width between about 7 mm and about 11 mm (e.g., about 9 mm). At location 108' the width narrows abruptly (e.g., within a distance of about 4 mm or less) to a width between about 1 mm and about 4 mm (e.g., about 2.5 mm). Described another way, at location 108', the width of bottom wall 104' is reduced between about 40 percent and about 90 percent, more preferably between about 50 percent and about 85 percent, and most preferably between about 60 percent and about 80 percent. These ranges have been found to provide a good fit for the majority of adult lower dental arches.

It is noted that the narrowing of bottom wall 104' of device 100' is not as pronounced or abrupt as in device 100 configured for placement over the upper dental arch. This is a result of general differences in the occlusal surface width between teeth of the upper dental arch relative to differences between teeth of the lower dental arch. The upper incisors are generally oriented more vertically relative to the occlusal plane than the lower incisors, which tend to be flared outward at a greater angle relative to a horizontal occlusal plane (e.g., about 87° versus about 78°). Providing the lower tray with a slightly wider bottom wall (e.g., about 2.5 mm) than the bottom wall of the upper tray (e.g., about 1.5 mm) has been found to improve the ease with which a variety of users are able to install the tray over the dental arch. For example, it is fairly common for the lower incisors to be somewhat crowded or twisted, for which the wider bottom wall is helpful. Devices of somewhat different geometries specifically configured for use over the upper or lower dental arches provide for much improved fit as compared to only providing a single device for use over both the upper dental arch as well as over the lower dental arch.

The posterior portion (e.g., near regions 109') of bottom wall 104' and labial-buccal wall 102' includes a transition portion between bottom wall 104' and labial-buccal wall 102' where the radius of curvature at the transition portion is greater than the radius of curvature at a transition portion between bottom wall 104' and lingual wall 106'. This difference in curvature on the lingual side versus the labial-buccal side of the tray accounts for the difference in angulation and orientation of the teeth, particularly the posterior teeth, on the labial-buccal tooth surfaces versus the lingual tooth surfaces. These curvature configurations allow the non-custom tray to better conform to the lower dental arch. Additional details of the configuration of the transition area between the bottom wall 104' and the labial-buccal wall 102' as compared to the transition area between the bottom wall 104' and the lingual wall 106' will be further described below in conjunction with FIG. 8B.

Figure 1C:
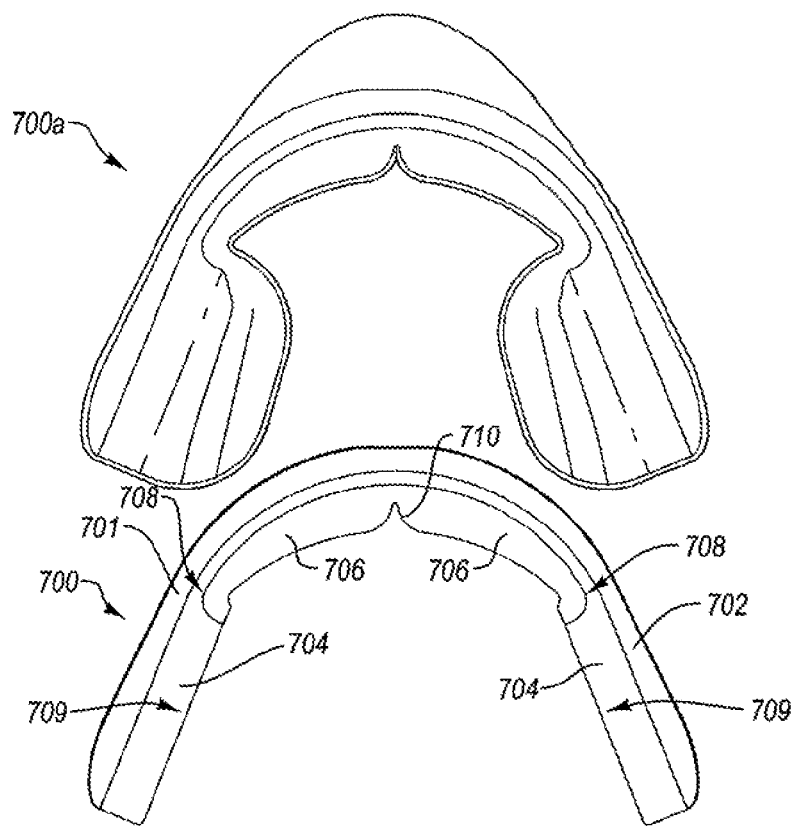
FIG. 1C is a perspective view of another exemplary dental treatment tray configured to fit over at least a portion of a person's upper dental arch, next to an associated exoskeleton.
Figure 1D:
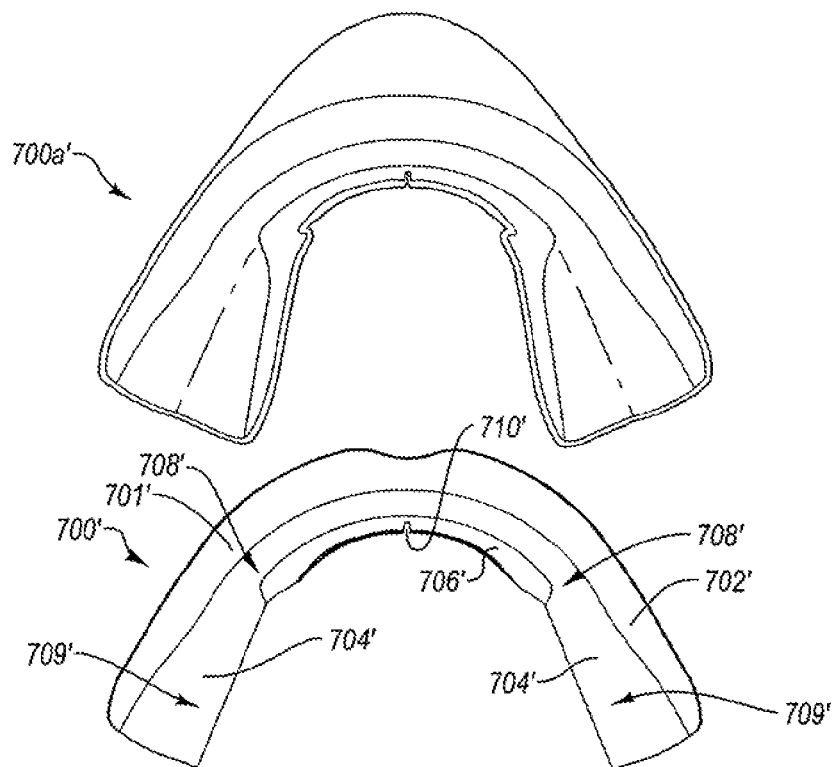
FIG. 1D is a perspective view of another exemplary dental treatment tray configured to fit over at least a portion of a person' lower dental arch, next to an associated exoskeleton.

FIGS. 1C-1D illustrate alternative dental treatment tray devices 700 and 700' configured for placement over the upper and lower dental arches, respectively. Each dental treatment tray device 700 and 700' is illustrated next to an associated support skeleton (700a and 700a', respectively). Dental treatment tray 700 is similar to dental treatment tray 100 in that it is configured for placement over a person's upper dental arch. Dental treatment tray 700 includes a barrier layer 701, a labial-buccal wall 702, a bottom wall 704, a lingual wall 706, and a notch 710. A principal difference between tray 700 and tray 100 is that lingual wall 706 terminates near (e.g., at or before) location 708. In other words, lingual wall 706 extends along the anterior portion of the tray so that wall 706 will be positioned adjacent to the anterior teeth during use, but no lingual coverage is provided to the posterior teeth because of the early termination of lingual wall 706. In addition the posterior portion 709 of bottom wall 704 may not be as wide as analogous wall 104 of tray 100. In other words, a posterior portion of lingual wall 706 and optionally a part of a posterior portion of bottom wall 704 may be cut away relative to tray 100 of FIG. 1A.

At locations 708, bottom wall 704 abruptly narrows. Locations 708 advantageously correspond to a transition from the posterior teeth (i.e., molars and bicuspids) to the anterior teeth (i.e., canines and incisors). If a portion of the posterior part of bottom wall 704 is cut away relative to tray 100 of FIG. 1A, the narrowing of bottom wall 704 may not be so pronounced as that of tray 100, although the narrowing of bottom wall 704 is still evident as seen in FIG. 1C. The effect of such an embodiment is that an enhanced, close fit is still provided at the transition from posterior teeth to anterior teeth, although the bottom wall may not cover the full occlusal surface width of the posterior teeth (i.e., because it has been narrowed relative to bottom wall 104 of tray 100). It has been found that an embodiment as illustrated in FIG. 1C may facilitate easier manipulation and positioning of the tray, as it is not necessary to manipulate or position a posterior portion of lingual wall 706 against the lingual side of the dental arch. Although the lingual wall 706 terminates so as to not cover the posterior teeth, the abrupt narrowing in the width of the bottom wall at a location corresponding to the transition from posterior to anterior teeth still results in an enhanced, closer fit and increased comfort when using the non-custom dental treatment tray as compared to a tray that does not include such an abrupt narrowing.

As seen in FIG. 1C, support skeleton 700a may be identical to support skeleton 100a of FIG. 1A. Alternatively, skeleton 700a may be configured as tray 700 with a terminated lingual wall and optionally a bottom wall that is also narrowed in a region corresponding to the posterior teeth. Providing a skeleton that includes a full length, non-terminated lingual wall and a full width bottom wall is useful during placement of tray 700 as it provides for better support to facilitate better control when positioning tray 700 over the upper dental arch.

Dental treatment tray 700' is similar to dental treatment tray 100' in that it is configured for placement over a person's lower dental arch. Dental treatment tray 700' includes a barrier layer 701', a labial-buccal wall 702', a bottom wall 704', a lingual wall 706', and a notch 710'. A principal difference between tray 700' and tray 100' is that lingual wall 706' terminates near (e.g., at or before) location 708'. In other words, lingual wall 706' extends along the anterior portion of the tray so that wall 706' will be positioned adjacent to the anterior teeth during use, but no lingual coverage is provided to the posterior teeth because of the early termination of lingual wall 706'. In addition, the posterior portion 709' of bottom wall 704' may not be as wide as analogous wall 104' of tray 100'. In other words, a posterior portion of lingual wall 706' and optionally a part of a posterior portion of bottom wall 704' may be cut away relative to tray 100' of FIG. 1B.

At locations 708', bottom wall 704' abruptly narrows. Locations 708' advantageously correspond to a transition from the posterior teeth (i.e., molars and bicuspids) to the anterior teeth (i.e., canines and incisors). If a portion of the posterior part of bottom wall 704' is cut away relative to tray 100' of FIG. 1B, the narrowing of bottom wall 704' may not be so pronounced as that of tray 100', although the narrowing of bottom wall 704' is still evident as seen in FIG. 1D. The effect of such an embodiment is that an enhanced, close fit is still provided at the transition from posterior teeth to anterior teeth, although the bottom wall may not cover the full occlusal surface width of the posterior teeth (i.e., because it has been narrowed relative to bottom wall 104' of tray 100'). It has been found that an embodiment as illustrated in FIG. 1D may facilitate easier manipulation and positioning of the tray, as it is not necessary to manipulate or position a posterior portion of lingual wall 706' against the lingual side of the dental arch. Although the lingual wall 706 terminates so as to not cover the posterior teeth, the abrupt narrowing in the width of the bottom wall at a location corresponding to the transition from posterior to anterior teeth still results in an enhanced, closer fit and increased comfort when using the non-custom dental treatment tray as compared to a tray that does not include such an abrupt narrowing.

As seen in FIG. 1D, support skeleton 700a' may be identical to support skeleton 100a' of FIG. 1B. Alternatively, skeleton 700a' may be configured as tray 700' with a terminated lingual wall and optionally a bottom wall that is also narrowed in a region corresponding to the posterior teeth. Providing a skeleton that includes a full length, non-terminated lingual wall and a full width bottom wall is useful during placement of tray 700' as it provides for better support to facilitate better control when positioning tray 700' over the lower dental arch.

Figure 1E:
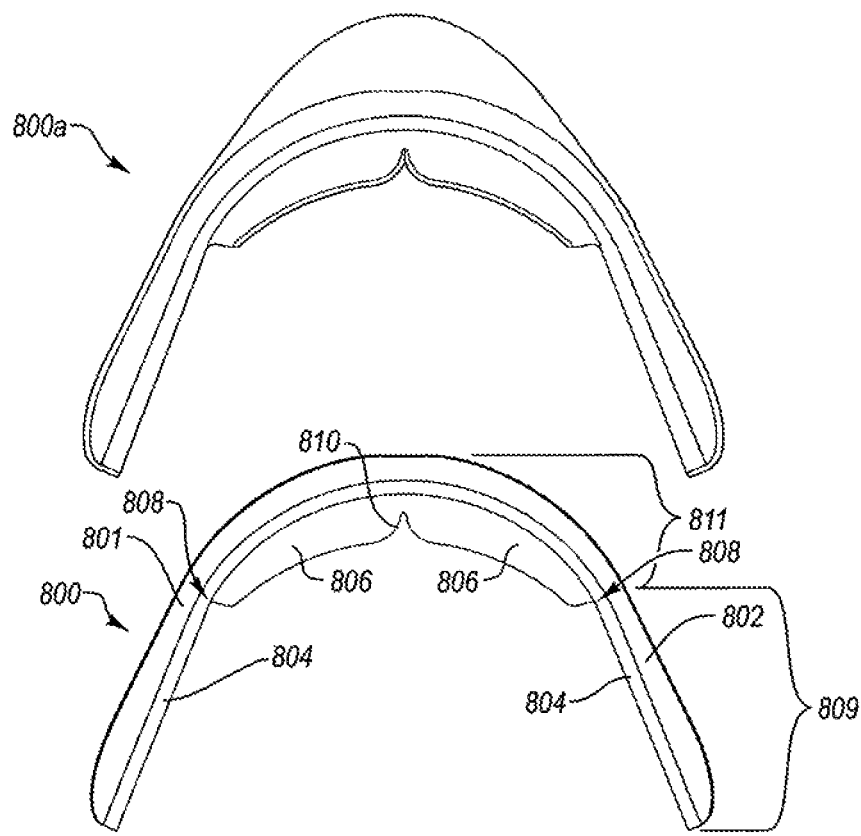
FIG. 1E is a perspective view of an exemplary dental treatment tray configured to fit over at least a portion of a person's upper dental arch, next to an optional exoskeleton, which has no lingual wall in the posterior region.
Figure 1F:
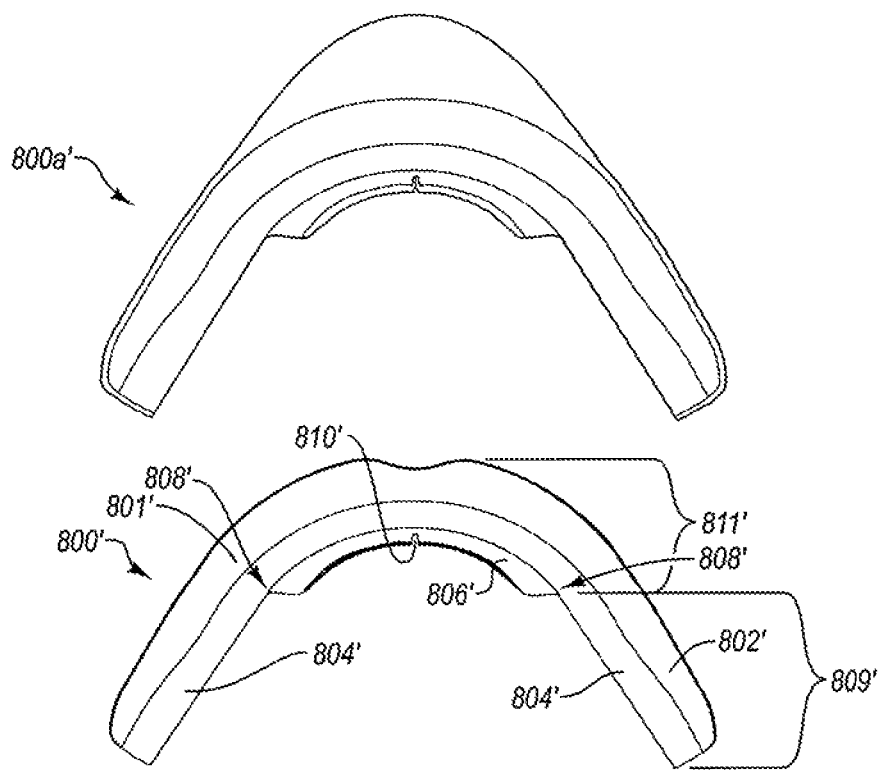
FIG. 1F is a perspective view of an exemplary dental treatment tray configured to fit over at least a portion of a person's lower dental arch, next to an optional exoskeleton, which has no lingual wall in the posterior region.

FIGS. 1E-1F illustrate alternative dental treatment tray devices 800 and 800' configured for placement over the upper and lower dental arches, respectively. Each dental treatment tray device 800 and 800' is illustrated next to an optional associated support skeleton (800a and 800a', respectively). Dental treatment tray 800 is similar to dental treatment tray 700 in that it is configured for placement over a person's upper dental arch. Dental treatment tray 800 includes a barrier layer 801, a labial-buccal wall 802, a bottom wall 804, a lingual wall 806, and a notch 810. Lingual wall 806 terminates at or before location 808 (e.g., corresponding to a location where the canine and first bicuspid meet). In other words, lingual wall 806 extends along the anterior region 811 of the tray 800 so that wall 806 will be positioned adjacent to the anterior teeth during use, but no lingual wall is present along the posterior region 809 of the tray because of the early termination of lingual wall 806.

A principal difference between tray 800 and tray 700 of FIG. 1C is that the width of bottom wall 804 within posterior portion 809 is typically less than or equal to the width of bottom wall 804 within anterior region 811 (e.g., nearly all of bottom wall 804 may be cut away relative to trays 100 and 700 of FIGS. 1A and 1C, respectively), as it may not be necessary or desirable to treat the occlusal and labial surfaces of the posterior teeth. Such a configuration reduces the tray wall surface area that must be kept adjacent to and adhered to the posterior teeth during treatment, as there is no labial wall in the posterior portion 809, and the surface area of bottom wall 804 within posterior portion 809 is greatly reduced relative to illustrated trays 100 and 700.

Although there is no abrupt width reduction in bottom wall 804 as in trays 100 and 700, a similar result of enhanced comfort and fit is still achieved. A principal purpose of reducing the bottom wall width at transition location 108 (see FIG. 1A) is to provide a bottom wall within the anterior region which is relatively narrow so as to be tailored to the occlusal width of the anterior teeth and a bottom wall within the posterior region which is substantially wider so as to be tailored to the occlusal width of the posterior teeth, although the wider width of the bottom wall within the posterior region may be absent, along with the posterior portion of the lingual wall, and achieve better non-custom fit. In tray 100, the transition between narrow and wide width occurs abruptly at location 108 (e.g., between the first bicuspid and the canine). Because the bottom wall snugly fits the occlusal width of both the anterior and posterior regions of the dental arch, pressure applied to the bottom wall within either region does not result in a pulling off of another portion of the bottom wall, which may otherwise be expected to occur if the bottom wall width were not configured to snugly fit the occlusal surface of the dental arch. Forming the tray such that the lingual wall and a substantial portion of the bottom wall are absent within the posterior region of the tray does not alter the ability of the remaining surfaces of the tray (i.e., the labial wall and the remaining portions of the bottom wall) to snugly fit against the labial and a portion of the occlusal tooth surfaces of the dental arch. In fact, it may further enhance fit even though the tray is non-custom by virtually eliminating the possibility of poor fit between the tray and a person's posterior teeth.

In this embodiment it is the actual width (which is relatively narrow relative to the occlusal tooth surfaces of the posterior teeth) of the bottom wall along the anterior region and at transition location 808 in combination with providing a lingual wall which terminates at or before location 808 that is important to the tray's ability to snugly fit over the dental arch. For example, bottom wall 804 has a width at location 808 which is between about 1 mm and about 3 mm (e.g., about 1.5 mm). This narrow width continues throughout the anterior region 811 of the tray so as to accommodate the occlusal surface width of the incisors. Rather than abruptly widening posterior to location 808, the width may remain substantially equal to the width at location 808 and anterior thereto, or even be further reduced such that the posterior portion of bottom wall 804 only covers a small portion of the occlusal surface of the posterior bicuspids and molars along the occlusal-labial edge of the dental arch. In such an embodiment, the narrow remaining portion of bottom wall 804 in the posterior region of tray 800 may simply act as a guide and anchor to aid in aligning the tray 800 over the dental arch, as little or no treatment of the posterior occlusal tooth surfaces is provided by such a tray 800. The posterior portion of bottom wall 804 laterally extends from labial wall 802 so as to act as a guide and anchor to the posterior portion of labial wall 802, which covers the labial tooth surfaces of the dental arch.

Similar to the embodiment illustrated in FIG. 1C, upper tray 800 may facilitate easier manipulation and positioning of the tray, as it is not necessary to manipulate or position a posterior portion of a lingual wall against the lingual side of the dental arch. Although lingual wall 806 terminates at or before location 808 so as to not cover the posterior teeth, the overall narrow width of bottom wall 804 along the anterior region 811 of the tray and up to location 808 still results in an enhanced, close, snug fit with increased comfort when using the non-custom dental treatment tray as compared to existing non-custom tray designs. The presence of lingual wall 806 along anterior region 811 and its absence within posterior region 809 further aids in providing a snug fit of the tray 800 against the occlusal tooth surfaces of the dental arch.

Referring to FIG. 1F, dental treatment tray 800' is similar to dental treatment tray 700' in that it is configured for placement over a person's lower dental arch. Dental treatment tray 800' includes a barrier layer 801', a labial-buccal wall 802', a bottom wall 804', a lingual wall 806' within the anterior region 811' of the tray, and a notch 810'. Similar to tray 800, lingual wall 806' terminates at or near location 808'. In other words, lingual wall 806' extends along the anterior region 811' of the tray so that wall 806' will be positioned adjacent to the anterior teeth during use, but no lingual coverage is provided to the posterior teeth because of the early termination of lingual wall 806'. Also similarly, bottom wall 804' may have its posterior portion cut away or otherwise absent relative to tray 700' of FIG. 1D so that the width of bottom wall 804' within posterior region 809' is less than or equal to the width of bottom wall 804' within anterior region 811' (e.g., nearly all of bottom wall 804' may be cut away relative to trays 100' and 700' of FIGS. 1B and 1D, respectively), as it may not be necessary or desirable to treat the occlusal and labial surfaces of posterior teeth. Such a configuration reduces the tray wall surface area that must be kept adjacent to and adhered to the posterior teeth during treatment, as there is no labial wall in the posterior portion 809', and the surface area of bottom wall within posterior portion 809' is greatly reduced relative to illustrated trays 100' and 700'.

Although there is no abrupt width reduction in bottom wall 804' as in trays 100' and 700', a similar result of enhanced comfort and fit is still achieved. As described above, a principal purpose of reducing the bottom wall width at transition location 108' (see FIG. 1B) is to provide a bottom wall within the anterior region of the tray which is relatively narrow so as to be tailored to the occlusal width of the anterior teeth and a bottom wall within the posterior region which is substantially wider so as to be tailored to the occlusal width of the posterior teeth. The transition between narrow and wide width occurs abruptly at location 108' (e.g., between the first bicuspid and the canine). Because the bottom wall snugly fits the occlusal width of both the anterior and posterior regions of the dental arch, pressure applied to the bottom wall within either region does not result in a pulling off of another portion of the bottom wall, which may otherwise be expected to occur if the bottom wall width were not configured to snugly fit the occlusal surface of the dental arch. Removing the lingual wall and a substantial portion of the bottom wall within the posterior region 809' of the tray does not alter the ability of the remaining surfaces of the tray 800' (i.e., the labial wall and the remaining portions of the bottom wall) to snugly fit against the labial and a portion of the occlusal tooth surfaces of the dental arch.

In other words, in such an embodiment it is the actual width (which is relatively narrow relative to the occlusal tooth surfaces of the posterior teeth) of the bottom wall along the anterior region 811' and at transition location 808' in combination with providing a lingual wall which terminates at or near location 808' that is important to the tray's ability to snugly fit over the dental arch. For example, bottom wall 804' has a width at location 808' which is between about 1 mm and about 4 mm (e.g., about 2.5 mm). This narrow width continues throughout the anterior region 811' of the tray so as to snugly accommodate the occlusal surface width of the incisors. Rather than abruptly widening posterior to location 808', the width may remain substantially equal to the width at location 808' and anterior thereto, or be even further reduced such that the posterior portion of bottom wall 804' only covers a small portion of the occlusal surface of the posterior bicuspids and molars along the occlusal-labial edge of the dental arch. In such an embodiment, the narrow remaining portion of bottom wall 804' in the posterior region of tray 800' may simply act as a guide and anchor to aid in aligning the labial wall 802' over the posterior portion of the labial tooth surfaces of the dental arch.

As seen in FIGS. 1E-1F, optional support skeletons 800a and 800a' may include a configuration similar to trays 800 and 800', respectively, including a terminated lingual wall and a bottom wall which has been cut away within the posterior region so as to not cover most of the posterior occlusal tooth surfaces.

Figure 2A:
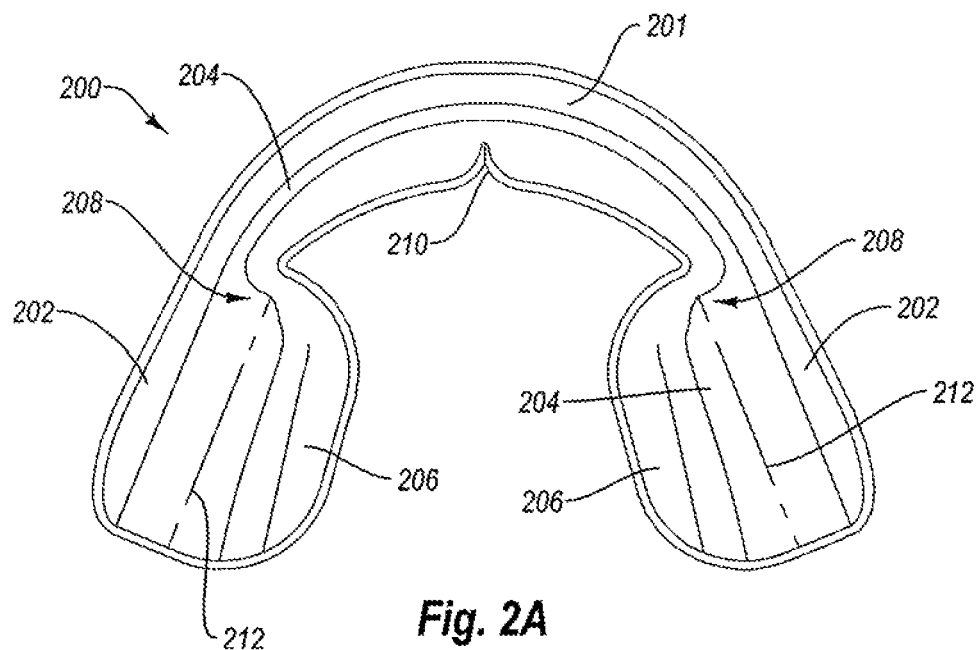
FIG. 2A is a perspective view of an exemplary mouth guard configured to fit over at least a portion of a person's upper dental arch.
Figure 2B:
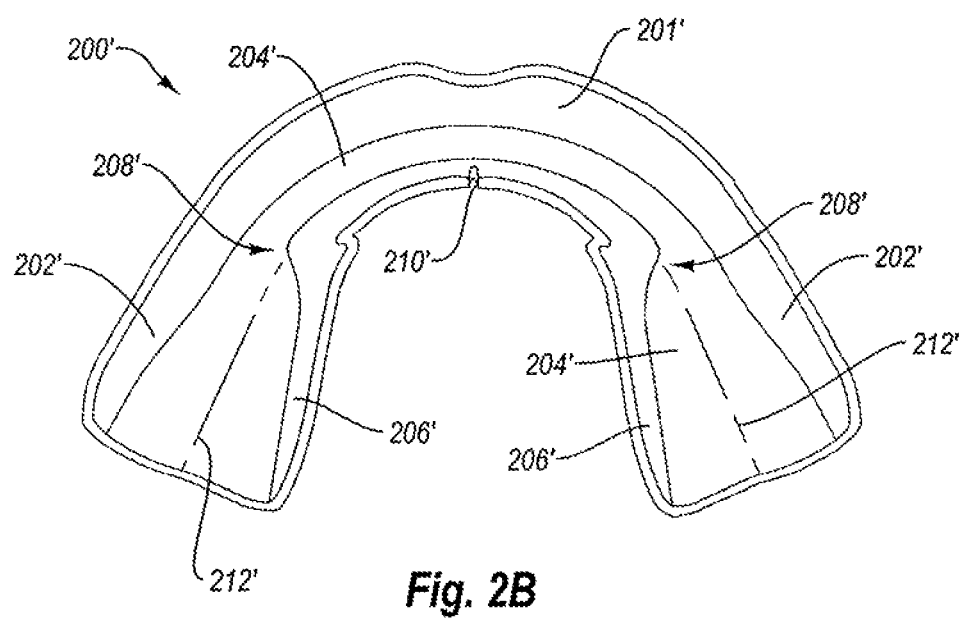
FIG. 2B is a perspective view of an exemplary mouth guard configured to fit over at least a portion of a person's lower dental arch.

FIGS. 2A-2B illustrate a set of mouth guards 200 and 200'. Mouth guard 200, similar to dental treatment tray 100, is configured for placement over a person's upper dental arch, while mouth guard 200' is configured for placement over a person's lower dental arch. Mouth guard 200 includes a barrier layer 201, a labial-buccal wall 202, a bottom wall 204, a lingual wall 206, a notch 210, and a pair of V-shaped indentations 212. At locations 208, bottom wall 204 abruptly narrows. Location 208 advantageously corresponds to a transition from the posterior teeth (i.e., molars and bicuspids) to the anterior teeth (i.e., canines and incisors). Because the posterior teeth have a significantly greater occlusal surface width or thickness as compared to the anterior teeth, abruptly narrowing the width of the bottom wall at a location corresponding to this transition results in an enhanced, closer fit and increased comfort when using the non-custom mouth guard. In addition, the radius of curvature along a transition portion between a posterior portion of bottom wall 204 and a posterior portion of lingual wall 206 is advantageously greater than the radius of curvature along a transition portion between a posterior portion of bottom wall 204 and a posterior portion of labial-buccal wall 202.

Mouth guard 200' of FIG. 2B is similar to dental treatment tray 100' as it is configured for placement over a person's lower dental arch. Mouth guard 200' includes a barrier layer 201', a labial-buccal wall 202', a bottom wall 204', a lingual wall 206', a notch 210', and a pair of V-shaped indentations 212'. At locations 208', bottom wall 204' advantageously abruptly narrows to result in an enhanced, closer, and more comfortable fit to the dental arch in the area of the first bicuspids and the canines. Along the posterior portion of mouth guard 200', the radius of curvature along a transition portion between bottom wall 204' and labial-buccal wall 202' is advantageously greater than the radius of curvature at a transition portion between bottom wall 204' and lingual wall 206'.

The mouth guards 200 and 200' are sufficiently thick and rigid so that no exoskeleton support is required when placing the mouth guard devices over the teeth. For example, the mouth guards preferably have a thickness between about 2 mm and about 5 mm, more preferably between about 2 mm and about 4 mm, and most preferably between about 2 mm and about 3 mm. Inclusion of one or more of the structural features described advantageously allows the non-custom mouth guards to better conform to the dental arch for which it is configured as compared to a non-custom mouth guard that does not include any such structural features. The non-custom mouth guards advantageously may be used without any required customization or fitting step as required with "boil and bite" mouth guards, while still providing a good fit to the dental arch. Alternatively, the mouth guards may be at least partially customized to the dental arch through heating followed by subsequent conforming to the dental arch (i.e., boil and bite). In such an embodiment, the presence of one or more of the described structural features enables the mouth guard to better conform to the teeth, particularly after customization, because the structural features provide a better fit to begin with, i.e., prior to any customization. Furthermore, because the structural features result in improved fit, less thickness is required to deliver any given level of protection and cushioning to the dental arch as the mouth guard has better contact so as to cradle the hard and soft tissues of the dental arch. Finally, the relatively thinner mouth guards are generally more comfortable to wear as compared to a thicker mouth guard.

Figure 3:
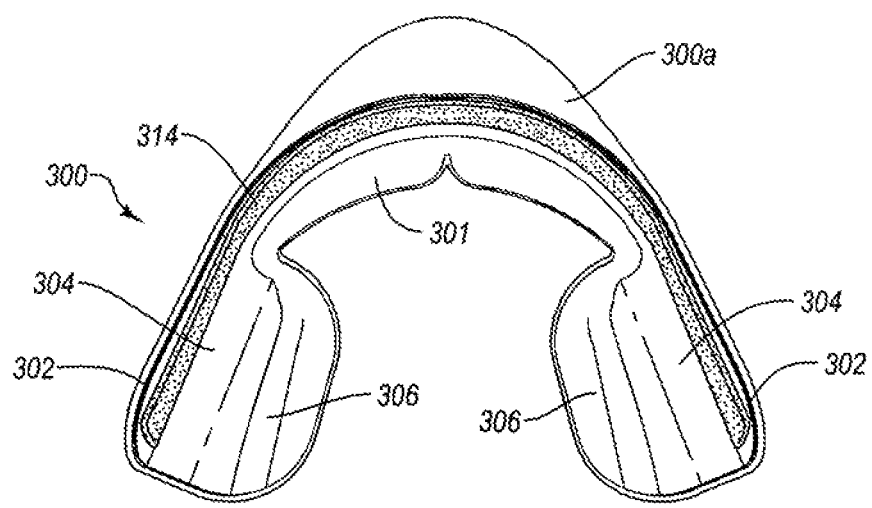
FIG. 3 is a perspective view of the dental treatment tray and exoskeleton of FIG. 1A with a substantially solid adhesive composition placed adjacent a wall of the tray.

FIG. 3 illustrates an example of a dental treatment tray 300 nested within an exoskeleton 300a, which provides support to tray 300. Tray 300 includes a moisture-resistant barrier layer 301 having a labial-buccal wall 302, a bottom wall 304, and a lingual wall 306. The tray 300 is held within and supported by exoskeleton 300a, which is helpful during placement of the tray over a dental arch. A substantially solid adhesive composition 314 is disposed adjacent to an inside surface of barrier layer 301 (e.g., adjacent to labial-buccal wall 302 and/or bottom wall 304). In one example, the adhesive composition 314 may be a dry insert having the same shape as the tray that is placed within the tray 300.

Figure 4:
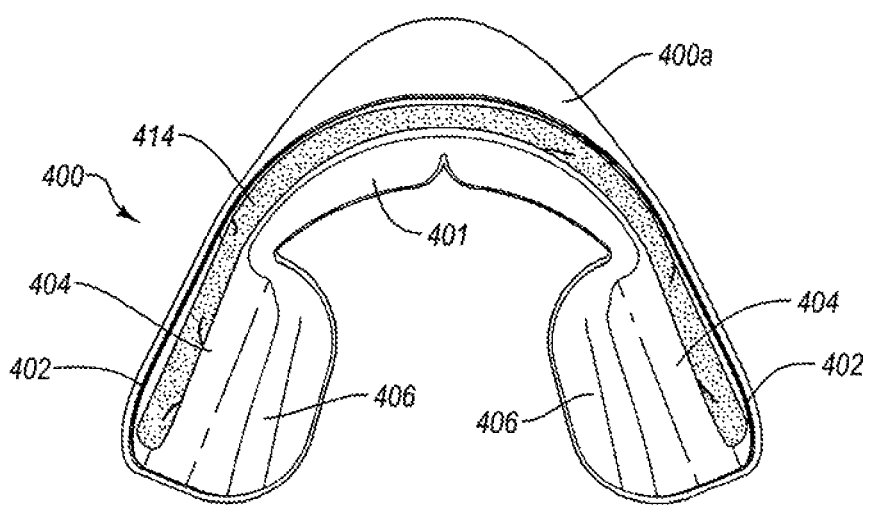
FIG. 4 is a perspective view of the dental treatment tray and exoskeleton of FIG. 1A with a gel treatment composition placed adjacent a wall of the tray.

FIG. 4 illustrates an example of another dental treatment tray 400 nested within an exoskeleton 400a. Tray 400 includes a moisture-resistant barrier layer 401 having a labial-buccal wall 402, a bottom wall 404, and a lingual wall 406. The tray 400 is held within and supported by exoskeleton 400a, which is helpful during placement of the tray over a dental arch. A gel treatment composition 414 is disposed adjacent to an inside surface of barrier layer 401 (e.g., adjacent to labial-buccal wall 402 and/or bottom wall 404). The treatment compositions (e.g., 314 and/or 414) may be pre-applied during manufacture and packaging of the dental treatment tray devices. Such a configuration advantageously eliminates any requirement for the user to dispense a treatment composition into the tray prior to use. Alternatively, the treatment compositions may be dispensed by the user into the tray just prior to use.

In some embodiments, more than one type of treatment and/or adhesive composition may be dispensed within the tray. For example, a substantially solid adhesive composition may be disposed adjacent the lingual wall for adhering the tray to the lingual tooth surface and a gel treatment composition may be disposed adjacent the labial-buccal wall, the bottom wall, and/or the lingual wall so as to contact the labial-buccal tooth surface, and optionally one or both of the occlusal and lingual tooth surfaces during treatment. In another example, one of the compositions may be intended to contact the gums, but to provide no treatment. Such a composition preferably contains no dental bleaching agent which otherwise may irritate the soft tissue surrounding the teeth (e.g., gingival tissue). Such a composition may advantageously act to reduce or prevent contact between the treatment composition containing a treatment agent and the person's soft tissue.

Figure 5:
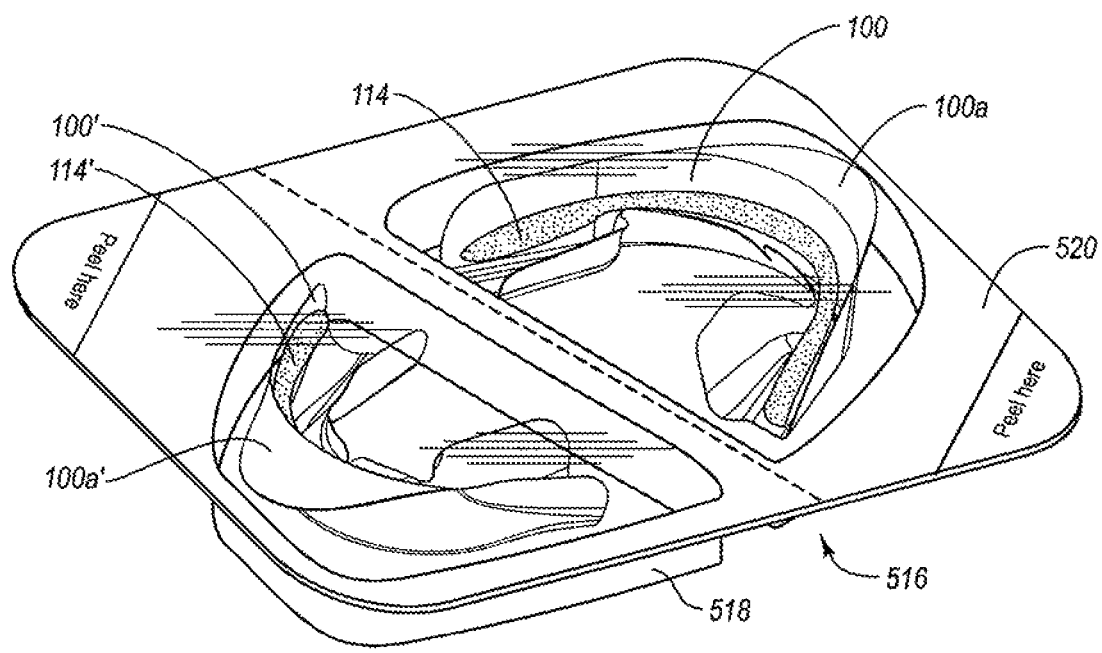
FIG. 5 illustrates a sealed protective package having a peelable cover that contains the dental treatment trays and exoskeletons of FIGS. 1A and 1B.

In order to protect one or more of the non-custom dental tray devices according to the invention from contaminants during storage and prior to use, the devices can be packaged within a sealed container or package. As illustrated in FIG. 5, the non-custom treatment tray 100, along with an associated exoskeleton 100a (i.e., configured for placement over the upper dental arch) can be sealed within a protective package 516 that includes a rigid support layer 518 and a peelable cover 520. As illustrated, package 516 may advantageously also include a non-custom treatment tray 100' and associated exoskeleton 100a' configured for placement over the lower dental arch, such that package 516 includes treatment tray devices for use over both the upper and lower dental arches. When it is desired to use the dental treatment tray devices, the peelable cover 520 is removed and the tray devices 100 and 100', along with the included support exoskeletons are removed or separated from support layer 518. In addition to, or instead of, the protective package 516, the tray devices may alternatively include a removable protective layer (not shown) that is temporarily placed adjacent to the interior surface of the treatment compositions 114 and 114'. When it is desired to use the tray device, the removable protective layer is removed so as to expose the interior surface of the adhesive composition and/or other treatment composition. In addition, prior to using the tray device, a gel or putty treatment composition may be applied to the inside of the device (e.g., as shown in FIG. 4).

In general, the thickness of any substantially solid adhesive composition layer and the barrier layer can be adjusted to yield a treatment tray device having a desired strength and flexibility. In order for the barrier layer to remain flexible so as to conform to a person's teeth, the barrier layer will generally have a thickness ranging from about 0.025 mm to about 2 mm, more preferably between about 0.05 mm and about 1 mm, and most preferably between about 0.1 and about 0.5 mm. When present, a substantially solid adhesive composition will generally have a thickness ranging from about 0.1 mm to about 3 mm. The thickness of the adhesive composition can also be selected depending on the intended duration of each bleaching session. In general, increasing the thickness of the adhesive composition layer where the adhesive composition includes a dental bleaching agent will provide a longer or more sustained release of active dental bleaching agent. By way of example, for short wear times, the adhesive composition layer including a dental bleaching agent will preferably have a thickness ranging from about 0.1 mm to about 0.5 mm. For intermediate wear times, the adhesive composition layer including a dental bleaching agent will preferably have a thickness ranging from about 0.5 mm to about 2 mm. For professional use and for overnight bleaching, the adhesive composition layer having a dental bleaching agent will preferably have a thickness ranging from about 2 mm to about 3 mm.

III. Exemplary Methods of Making Non-Custom Dental Tray Devices

According to one method of manufacturing an exemplary treatment tray device, an adhesive composition is made by first forming a flowable composition that is later dried to form a substantially solid adhesive composition. This may be performed by heating or otherwise causing one or more volatile solvents to be driven off by evaporation, thus leaving behind a substantially solid composition. The drying process may be performed before or after the adhesive composition is placed into contact with the barrier layer.

According to one embodiment, dental treatment tray devices can be made by spreading a flowable adhesive composition onto the surface of a large or continuous polymeric sheet. The polymeric sheet and adhesive composition are then placed into a forced air oven, other appropriate desiccation device, or allowed to dry in ambient conditions. Drying the sheet and adhesive composition drives off a substantial portion of the ethanol or other solvent used to form the flowable adhesive composition. Removal of the volatile solvent yields a substantially solid adhesive composition. Thereafter, individual dental treatment tray devices can be molded, such as by vacuum forming, pressing or stamping from the coated polymeric sheet and then separated into individual dental treatment tray devices suitable for placement over a person's teeth.

Alternatively, a flowable adhesive composition or a substantially solid adhesive composition can be molded or shaped into a desired tray-like configuration. Thereafter, a barrier layer may be attached or applied to an outer surface of the adhesive composition layer. In this embodiment, the barrier layer may initially comprise a flowable barrier material or precursor that is later cured or hardened, such as by removing a solvent by evaporation, by chemical or light curing, or by cooling a thermoplastic melt.

In yet another embodiment of the invention, a barrier layer having a labial-buccal wall, a lingual wall, and a bottom wall can be coated with a flowable adhesive composition. The adhesive composition is then heated together with the barrier layer or otherwise allowed to dry in order to form a substantially solid adhesive composition. This process can be performed during commercial manufacture of the dental treatment tray devices or by an end user.

Sticky viscous gels, less viscous gels, and/or highly viscous putties may be manufactured separate from the barrier layer. They may be applied to the barrier layer or an adhesive composition prior to packaging, if desired. Alternatively, the dental treatment tray devices can be provided with a separate gel or putty which the end user may apply.

The dental treatment tray devices may be placed within an optional exoskeleton during the manufacturing process prior to packaging, if desired. Alternatively, the tray-shaped dental treatment devices may be provided with a separate exoskeleton, or without an exoskeleton, as desired (e.g., a substantially solid adhesive composition may provide sufficient strength, support, and rigidity to the barrier layer, eliminating the need for an exoskeleton).

In the case of the relatively thick mouth guards, individual mouth guard devices can be molded (e.g., vacuum formed, pressed, or stamped) from a large sheet of polymer material, after which the mouth guard devices may be separated and packaged. Such a package may contain a mouth guard configured for use over the upper dental arch and a mouth guard configured for use over the lower dental arch).

IV. Exemplary Methods of Using Non-Custom Dental Treatment Tray Devices

The dental tray devices according to the invention can be designed to be worn for any desired time period. In the case of a dental treatment tray, increasing the concentration of dental bleaching agent in the treatment composition(s) generally reduces the bleaching time required to effect bleaching. Nevertheless, due to the extremely comfortable fit between the inventive non-custom dental treatment trays and the person's teeth, it is possible to wear such devices for extended periods of time in order to ensure more uniform bleaching. Especially with respect to dental treatment trays including a substantially solid adhesive composition layer, they may be designed to be worn while performing normal daily activities, such as talking, eating, drinking, smoking, coughing, smiling, frowning, grimacing, or while sleeping. This greatly decreases their intrusiveness into everyday activities compared to conventional bleaching strips, which do not reliably adhere to teeth, or intrusive bleaching devices such as large, bulky bleaching dental appliances.

Figure 6A:
FIG. 6A illustrates a person placing a dental treatment tray according to the invention over the upper dental arch.
Figure 6B:
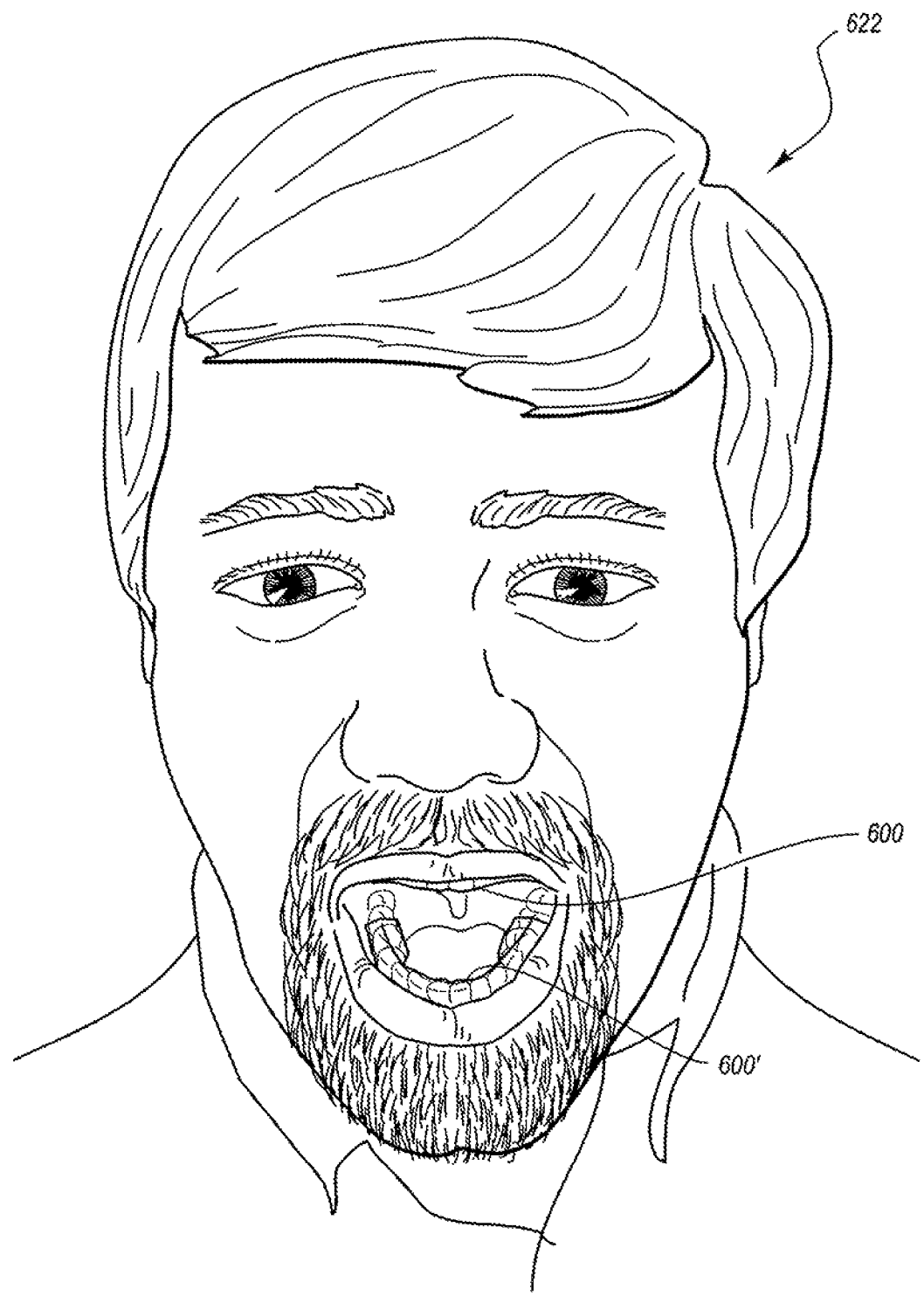
FIG. 6B illustrates a person having placed a dental treatment tray according to the invention over the lower dental arch, with a dental treatment tray already placed over the upper dental arch.

FIG. 6A illustrates a person 622 placing a dental treatment tray 600 over the person's upper dental arch using an exoskeleton as a support. FIG. 6B illustrates the person 622 placing a dental treatment tray 600' over the person's lower dental arch after having placed the tray 600 over the upper dental arch. It will be appreciated, however, that the dental treatment tray devices can be placed over a person's upper and lower dental arches in any desired order.

Figure 7A:
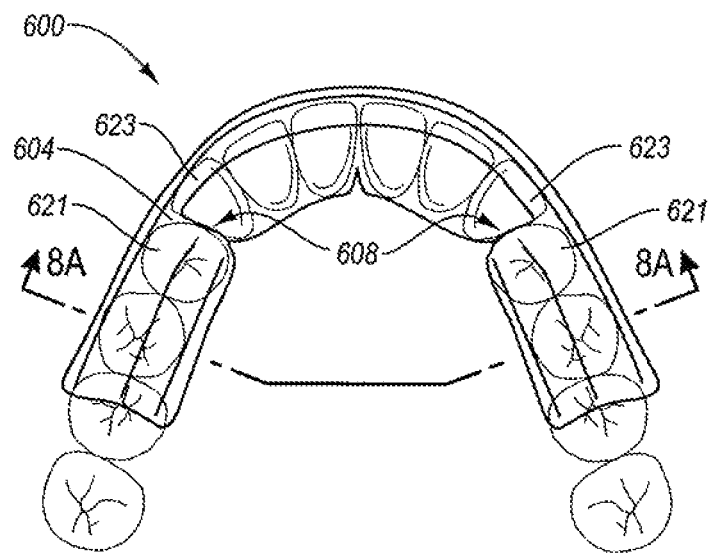
FIG. 7A is a close up top view of the dental treatment tray shown in FIG. 6B placed over a persons upper dental arch showing how the width of the bottom wall is configured to tuck into the abrupt narrowing of occlusal width between a person's first bicuspids and canines.
Figure 7B:
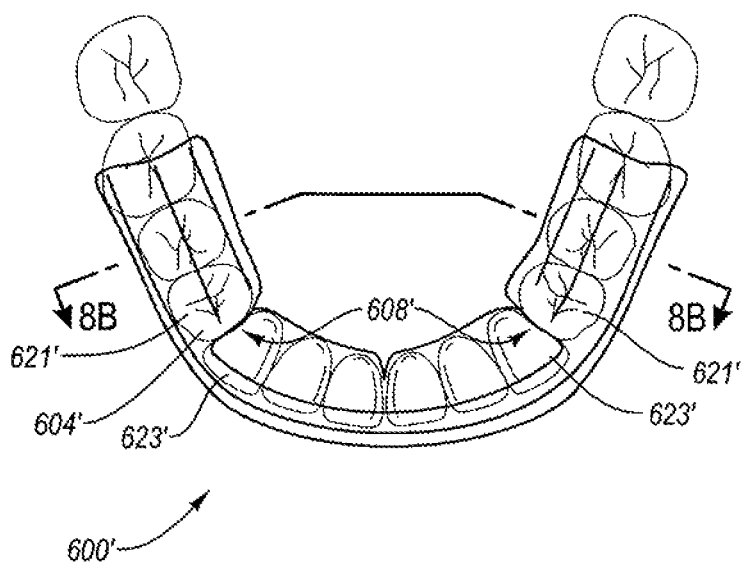
FIG. 7B is a close up top view of the other dental treatment tray shown in FIG. 6B placed over a persons lower dental arch showing how the width of the bottom wall is configured to tuck into the abrupt narrowing of occlusal width between a person's first bicuspids and canines.

The dental treatment tray devices 600 and 600' include a narrowing of bottom wall 604 at locations 608 and 608', respectively. FIGS. 7A and 7B illustrate how the narrowing of the bottom wall helps the bottom wall better conform to abrupt changes in the occlusal surface diameter, of the posterior teeth as compared to the anterior teeth. This abrupt change is most apparent at a location where the first bicuspid meets the canine (i.e., locations 608 and 608'). FIG. 7A shows a view of the upper dental arch from an occlusal perspective, so as to better illustrate how the occlusal surface of the molars and bicuspids is substantially greater in surface area, diameter, and width as compared to the occlusal surface of the canines and incisors. An abrupt tuck or narrowing of bottom wall 604 occurs between the first bicuspids 621 and canines 623 on each side of the upper dental arch, which allows the bottom wall and tray device 600 to better conform to the topology and shape of the teeth.

FIG. 7B shows a view of the lower dental arch, also from an occlusal perspective, so as to better illustrate how the occlusal surface of the molars and bicuspids is substantially greater in surface area, diameter, and width relative to the occlusal surfaces of the canines and incisors. An abrupt tuck or narrowing of bottom wall 604' occurs between first bicuspids 621' and canines 623' on each side of the upper dental arch, which allows the bottom wall and tray device 600' to better conform to the topology and shape of the teeth of the dental arch. It will further be noted that the teeth of the lower dental arch are substantially smaller than the teeth of the upper dental arch, particularly when comparing corresponding bicuspids, canines, and incisors. As already described, the overall dimensions of tray 600' generally are somewhat smaller than those of tray 600 to account for these differences.

Figure 8A:
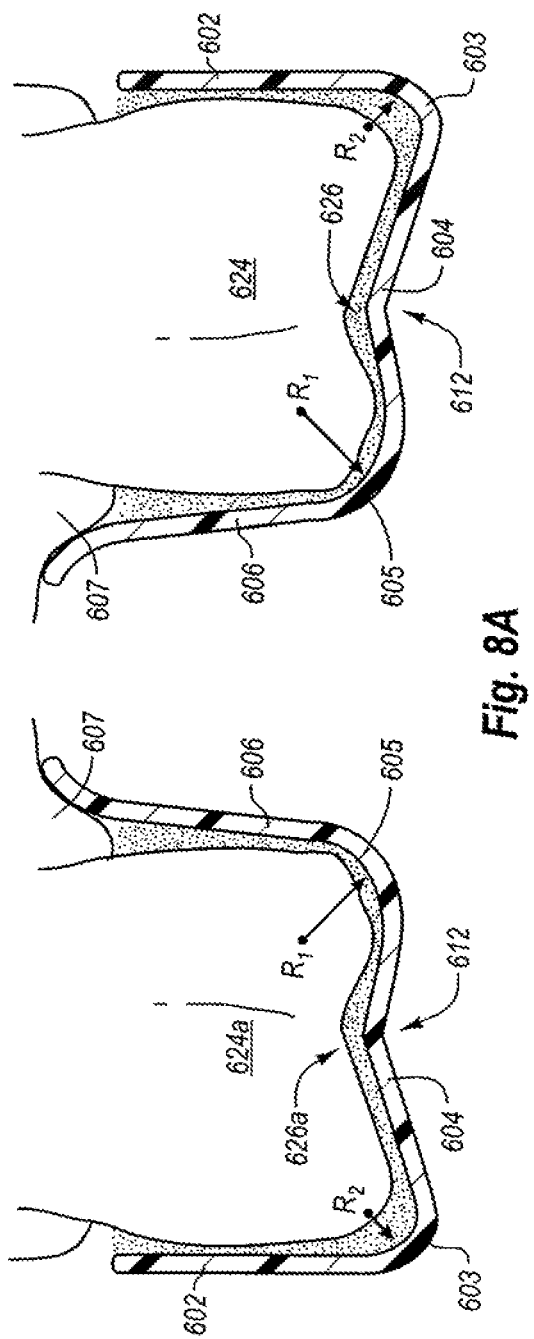
FIG. 8A is a close up cross sectional view of the dental treatment tray and upper dental arch of FIG. 7A showing that the transition portion between the bottom wall and the lingual wall has a radius of curvature that is larger than the radius of curvature of the transition portion between the bottom wall and the labial-buccal wall.

FIG. 8A is a close up cross sectional view illustrating how the transition portion 605 between bottom wall 604 and lingual wall 606 has a radius of curvature $R_1$ that is larger than the radius of curvature $R_2$ of the transition portion 603 between bottom wall 604 and labial-buccal wall 602. Radius of curvature $R_1$ is preferably between about 65 mm and about 200 mm, more preferably between about 100 mm and about 160 mm, and most preferably between about 115 mm and about 140 mm. Radius of curvature $R_2$ is preferably between about 15 mm and about 55 mm, more preferably between about 20 mm and about 50 mm, and most preferably between about 30 mm and about 40 mm. The transition from occlusal to lingual tooth surfaces of the posterior teeth of the upper dental arch is typically more gently curved than the transition from occlusal to labial-buccal tooth surfaces of the posterior teeth of the upper dental arch. Moreover, the teeth of the upper dental arch, particularly the upper posterior teeth, are generally angled or oriented in an outward direction (i.e., the longitudinal axis of each of the teeth of the upper dental arch is angled slightly in a labial-buccal direction from the vertical). For these reasons, providing a radius of curvature $R_1$ that is greater than $R_2$ results in a better fit between the non-custom tray device and the upper dental arch. In addition, lingual wall 606 includes an "S" type curve to advantageously provide a more comfortable fit against the lingual gum tissue 607.

Figure 8B:
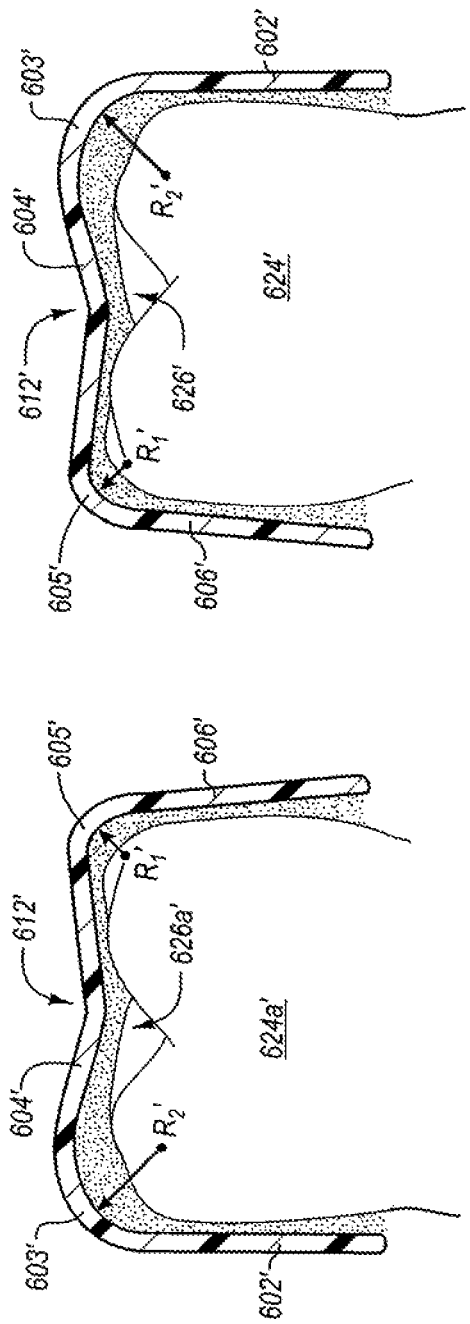
FIG. 8B is a close up cross sectional view of the dental treatment tray and lower dental arch of FIG. 7B showing that the transition portion between the bottom wall and the labial-buccal wall has a radius of curvature that is larger than the radius of curvature of the transition portion between the bottom wall and the lingual wall.

FIG. 8B is a close up cross sectional view illustrating how the transition portion 603' between bottom wall 604' and labial-buccal wall 602' has a radius of curvature $R_2'$ that is larger than the radius of curvature $R_1'$ of the transition portion 605' between bottom wall 604' and lingual wall 606'. Radius of curvature $R_1'$ is preferably between about 15 mm and about 45 mm, more preferably between about 20 mm and about 40 mm, and most preferably between about 30 mm and about 35 mm. Radius of curvature $R_2'$ is preferably between about 30 mm and about 85 mm, more preferably between about 40 mm and about 75 mm, and most preferably between about 50 mm and about 60 mm. The transition from occlusal to labial-buccal tooth surfaces of the posterior teeth of the lower dental arch is typically more gently curved than the transition from occlusal to lingual tooth surfaces of the posterior teeth of the lower dental arch. Moreover, the teeth of the lower dental arch, particularly the lower posterior teeth, are generally angled or oriented in an inward direction (i.e., the longitudinal axis of each of the teeth of the lower dental arch is angled slightly in a lingual direction from the vertical). For these reasons, providing a radius of curvature $R_2'$ that is greater than $R_1'$ results in a better fit between the non-custom tray device and the lower dental arch.

Furthermore, each bottom wall 604 and 604' includes a V-shaped indentation 612, 612' for insertion into the depression between the occlusal peaks of the posterior teeth (i.e., the bicuspids and molars). As seen, upper second bicuspids 624 and 624a and lower second bicuspids 624' and 624a' include depressions 626, 626a, and 626', 626a' respectively, into which V-shaped indentations 612 and 612' are configured to be inserted. This results in better conformity between the dental treatment trays 600 and 600' and the posterior teeth (i.e., bicuspids and molars), even when downward pressure is applied to bottom walls 604 and 604'.

In the absence of such indentations, the bottom wall of the treatment device may have a tendency to span the posterior teeth like a bridge between the generally higher outer edges, thereby leaving a gap between the bottom walls 604 and 604' and the surface of the posterior teeth between the outer edges. Permitting such a gap may inhibit or prevent bleaching of the depressed bicuspid and molar surfaces. Moreover, a bottom wall that is stretched between the outer surfaces so as to leave a gap over the posterior teeth depressions may result in inadvertent dislodgment of the treatment tray devices when the upper and lower bicuspids and/or molars are brought together. For example, if the bottom wall 604, 604' of a treatment tray device is pushed into the bicuspid/molar depressions by the opposing bicuspids and/or molars, the labial-buccal and/or bottom walls may be pulled down across the tooth surfaces to compensate for this effective lengthening of the bottom wall 604, 604' in the vicinity of the patient's posterior teeth.

To remove the dental treatment tray device, a user can pry open a corner of the barrier layer using a fingernail or rigid tool and then pull the remainder off. Any residual adhesive composition or gel or putty treatment composition that remains adhered to the person's teeth can be removed by washing or flushing water over the person's teeth, and/or by brushing. Although the adhesive compositions are very adhesive to teeth when protected from excessive moisture, they can be formulated to quickly breakdown and dissolve when flushed with excess water and/or by gentle mechanical action (e.g., brushing).

The dental treatment tray devices can be worn for as little as a few minutes and as long as several hours. By way of example, not limitation, a typical bleaching session of fast duration may last from about 10 to about 30 minutes. A bleaching session of intermediate duration may last from about 30 minutes to about 2 hours. A bleaching session of long duration, including professional bleaching or overnight bleaching while a person is sleeping, may last from about 2 hours to about 12 hours.

Bleaching sessions may be repeated as many times as are needed to obtain a desired degree of whitening. In some cases, a clinical whitening effect has been observed after only 1-3 whitening sessions. A typical bleaching regimen will preferably include 1-20 bleaching sessions, more preferably 2-15 bleaching sessions, and most preferably 3-10 bleaching sessions.

V. Exemplary Kits including Multiple Dental Tray Devices

For convenience of use, multiple dental treatment tray devices may be packaged together and sold as a kit. In one embodiment, the number of pairs of treatment trays (i.e., one upper tray and one lower tray) provided with each kit will equal the number of sessions that represent a prescribed bleaching regimen.

To efficiently use the space within a kit package, multiple dental treatment tray devices can be stacked or interested together. The devices can be sealed collectively or individually as desired. A protective package 516 is depicted in FIG. 5. The treatment tray devices may optionally contain a removable protective layer on an interior surface to protect the adhesive composition from contamination or moisture.

It is within the scope of the invention to provide exoskeletons, barrier layers, gel or putty treatment compositions, and/or adhesive compositions that are initially separate and that are brought together by the end user. For example, the adhesive composition may be a dry insert that is placed into the inventive tray-shaped barrier layer, with or without actually adhering the adhesive composition to the barrier layer. Alternatively, a flowable adhesive composition can be placed within a tray-shaped barrier layer with structural features and allowed to dry prior to placement of the finished tray-shaped dental treatment device over the person's teeth.

VI. Examples of the Preferred Embodiments

Following is an example of a dental bleaching composition and a dental treatment tray device that has been manufactured according to the invention. Additional examples of treatment compositions and barrier layer materials that may be used are disclosed in U.S. Pat. No. 7,074,042, hereby incorporated by reference with respect to examples of barrier layer materials and treatment compositions. The exemplary formulations and manufacturing conditions are given by way of example, and not by limitation, in order to further illustrate dental treatment tray devices that have been found to be useful for bleaching a person's teeth. Unless otherwise indicated, all percentages are by weight.

Example 1

An initially flowable adhesive composition suitable for use in manufacturing a substantially solid adhesive composition was formed by mixing together the following components:

| | |
|---|---:|
| Ethanol | 31.95% |
| Water | 10% |
| Polyvinyl Pyrrolidone (M.W. = 1.3 million) | 27% |
| Polyvinyl Pyrrolidone (M.W. of about 60,000) | 10% |
| Sodium Laurel Sulfate | 0.5% |
| Glycerine | 15% |
| Sucralose 25% solution | 0.5% |
| Peach Flavor | 4% |
| Potassium Nitrate | 0.8% |
| Sodium Fluoride | 0.25% |

The resulting adhesive composition was spread over the surface of a large flat sheet formed of 80% ethyl vinyl acetate and 20% polypropylene. The EVA/PP sheet had a thickness of about 0.15 mm. The adhesive composition was spread using a skreeding device. The coated sheet was heated in a forced air oven until the adhesive composition dried. The coated sheet was removed from the oven and inspected. The adhesive composition had dried sufficiently so as to form a substantially solid layer on the surface of the polymer sheet. The adhesive composition was dry to the touch, but became very sticky when touched by a wet object. After drying, the adhesive composition film was reduced to approximately one-third of its original thickness when wet.

The coated sheet was thermoformed into dental treatment tray devices with the dry adhesive composition on the inside surface of the tray devices. Individual tray-shaped devices were cut out using dye cutting tools. A laser could alternatively be used for cutting. The tray-shaped devices included a labial-buccal wall, a lingual wall, and a bottom wall in which the width of the bottom wall was abruptly narrowed at a location corresponding to where the first bicuspids meet the canines so as to help the bottom wall better conform to abrupt changes in the diameter and occlusal surface width of a person's teeth, particularly where the bicuspids and canines meet. The tray-shaped devices configured for placement over the upper dental arch further included a transition portion between the bottom wall and the lingual wall having a larger radius of curvature as compared to a radius of curvature at a transition portion between the bottom wall and the labial-buccal wall. The tray-shaped devices configured for placement over the lower dental arch further included a transition portion between the bottom wall and the labial-buccal wall having a larger radius of curvature as compared to a radius of curvature at a transition portion between the bottom wall and the lingual wall.

A bleaching gel treatment composition for use with the dental treatment tray devices was prepared by mixing together the following components:

| | |
|---|---|
| Water | 22.5% |
| EDTA Disodium | 0.1% |
| Carbamide Peroxide | 18.5% |
| Sucralose 25% solution | 0.75% |
| Glycerine | 41.6% |
| Carbopol 974 | 5.3% |
| Sodium Hydroxide 50% solution | 2.25% |
| Polyvinyl Pyrrolidone (M.W. = 1.3 million) | 2% |
| Carboxymethyl Cellulose | 4% |
| Watermelon Flavor | 3% |

The dental treatment tray devices were placed in a holding device, and a bead of bleaching gel treatment composition was spread along the labial-buccal wall of the bleaching tray devices. Each tray-shaped device was then transferred to an exoskeleton.

The dental treatment tray devices were tested by placing them over a person's teeth. The residual saliva present on the tooth surfaces moistened the exposed surface of the adhesive composition and caused it to become sticky and very adhesive to teeth almost immediately. The non-custom dental treatment tray devices were pressed against the teeth, which caused them to conform to the natural irregularities of the dental arch and adhere firmly against the teeth.

In the tray configured for placement over the upper dental arch, the bottom wall had it greatest width of about 10 mm across the portion adapted to receive the bicuspids and/or molars. At a location corresponding to a transition from the first bicuspids to the canines, the bottom wall narrowed to a width of about 1.5 mm. The narrowing of the bottom wall on both the right and left sides corresponding to a location where the first bicuspid meets the canine helped the bottom wall better conform to abrupt changes in the occlusal surface width of a person's teeth, particularly where the bicuspids and canines meet. The transition portion between the bottom wall and the lingual wall had a radius of curvature of about 130 mm, while the transition portion between the bottom wall and the labial-buccal wall had a radius of curvature of about 35 mm. This difference in curvature of the transition portions between the bottom wall and the other walls resulted in a good fit between the non-custom tray device and the upper dental arch.

In the tray configured for placement over the lower dental arch, the bottom wall had it greatest width of about 9 mm across the portion adapted to receive the bicuspids and/or molars. At a location corresponding to a transition from the first bicuspids to the canines, the bottom wall narrowed to a width of about 2.5 mm. The narrowing of the bottom wall on both the right and left sides corresponding to a location where the first bicuspid meets the canine helped the bottom wall better conform to abrupt changes in the occlusal surface width of a person's teeth, particularly where the bicuspids and canines meet. The transition portion between the bottom wall and the lingual wall had a radius of curvature of about 32 mm, while the transition portion between the bottom wall and the labial-buccal wall had a radius of curvature of about 57 mm. This difference in curvature of the transition portions between the bottom wall and the other walls resulted in a good fit between the non-custom tray device and the lower dental arch.

The dental treatment tray devices were worn for varying time periods ranging from several minutes to several hours without becoming dislodged. In some cases a noticeable bleaching effect was detected after just one bleaching session (e.g., a 2-hour bleaching session). In all cases, noticeable bleaching was detected after 1-3 bleaching sessions.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A pre-shaped, non-customized dental tray device suitable for placement over at least a portion of a person's dental arch, the dental tray device comprising:

a generally horseshoe-shaped moisture resistant barrier layer configured to substantially correspond to the curvature of a person's dental arch and having sufficient flexibility without heating in boiling water so as to readily conform to a plurality of differently sized dental arches corresponding to different people without customization;

the barrier layer having an anterior region that at least partially covers anterior teeth surfaces when worn and a posterior region that at least partially covers posterior teeth surfaces when worn;

the barrier layer being substantially devoid of structures corresponding to the size and shape of a person's unique dentition so that the barrier layer is designed to comfortably fit over a plurality of differently-sized and/or shaped teeth corresponding to different people; and the barrier layer having a labial-buccal wall in the posterior and anterior regions, a lingual wall in the anterior region but not the posterior region, and a bottom wall interposed between the labial-buccal wall and the lingual wall in the anterior region and extending laterally relative to the labial-buccal wall in the posterior region, wherein a width of the bottom wall in the posterior region is equal to or less than a width of the bottom wall in the anterior region.

2. A pre-shaped, non-customized dental tray device as in claim 1, wherein the dental tray device is configured for placement over the upper dental arch and wherein the width of the bottom wall in the anterior region is between about 1 and about 3 mm.

3. A pre-shaped, non-customized dental tray device as in claim 1, wherein the dental tray device is configured for placement over the upper dental arch and wherein the width of the bottom wall in the anterior region is about 1.5 mm.

4. A pre-shaped, non-customized dental tray device as in claim 1, wherein the dental tray device is configured for placement over the lower dental arch and wherein the width of the bottom wall in the anterior region is between about 1 and about 4 mm.

5. A pre-shaped, non-customized dental tray device as in claim 1, wherein the dental tray device is configured for placement over the lower dental arch and wherein the width of the bottom wall in the anterior region is about 2.5 mm.

6. A pre-shaped, non-customized dental tray device as in claim 1, wherein the barrier layer has a thickness less than about 2 mm.

7. A pre-shaped, non-customized dental tray device as in claim 1, wherein the barrier layer has a thickness less than about 1 mm.

8. A pre-shaped, non-customized dental tray device as in claim 1, wherein the barrier layer has a thickness less than about 0.5 mm.

9. A pre-shaped, non-customized dental tray device as in claim 1, wherein the barrier layer comprises at least one material selected from the group consisting of polyolefins, polyethylene (PE), high density polyethylene (HDPE), low density polyethylene (LDPE), ultra low density polyethylene (ULDPE), polypropylene, polytetrafluoroethylene (PTFE), waxes, paraffins, metal foils, ethylene-vinyl acetate copolymers (EVA), ethylene-vinyl alcohol copolymers (EVAL), polycaprolactone (PCL), polyvinyl chloride (PVC), polyesters, polyethylene terephthalate (PET), polycarbonates, polyamides, polyurethanes, and polyesteramides.

10. A pre-shaped, non-customized dental tray device as in claim 9, wherein the barrier layer comprises multiple layers comprising two or more of the at least one material.

11. A pre-shaped, non-customized dental tray device as in claim 9, wherein the barrier layer comprises a polymeric blend.

12. A pre-shaped, non-customized dental tray device as in claim 9, wherein the barrier layer comprises a blend of polyolefin and paraffin wax.

13. A pre-shaped, non-customized dental tray device as in claim 9, further comprising at least one of a plasticizer, flow additive, or filler to modify properties of one or more polymer materials forming the barrier layer.

14. A pre-shaped, non-customized dental tray device as defined in claim 1, wherein the barrier layer comprises at least one member selected from the group consisting of cellulosic ethers, cellulose acetate, polyvinyl acetate, polyvinyl alcohol, shellac, chemical-cure materials, light-cure materials, methacrylate resins, acrylate resins.

15. A pre-shaped, non-customized dental tray device as in claim 1, wherein the lingual wall further includes a notch positioned so that the dental tray device more easily spreads open or compresses in a region near a person's incisors.

16. A pre-shaped, non-customized dental tray device as in claim 1, further comprising a support skeleton positionable adjacent to the barrier layer prior to placement over the person's teeth so as to help maintain the barrier layer in a tray-like configuration and/or facilitate placement of the barrier layer over the person's teeth.

17. A pre-shaped, non-customized dental treatment device, comprising:
 a dental tray device composed of:
  a generally horseshoe-shaped moisture resistant barrier layer configured to substantially correspond to the curvature of a person's dental arch and having sufficient flexibility without heating in boiling water so as to readily conform to a plurality of differently sized dental arches corresponding to different people without customization;
  the barrier layer having an anterior region that at least partially covers anterior teeth surfaces when worn and a posterior region that at least partially covers posterior teeth surfaces when worn;
  the barrier layer being substantially devoid of structures corresponding to the size and shape of a person's unique dentition so that the barrier layer is designed to comfortably fit over a plurality of differently-sized and/or shaped teeth corresponding to different people; and
  the barrier layer having a labial-buccal wall in the posterior and anterior regions, a lingual wall in the anterior region but not the posterior region, and a bottom wall interposed between the labial-buccal wall and the lingual wall in the anterior region and extending laterally relative to the labial-buccal wall in the posterior region, wherein a width of the bottom wall in the posterior region is equal to or less than a width of the bottom wall in the anterior region; and
 a dental treatment composition adjacent to the dental tray device.

18. A pre-shaped, non-customized dental treatment device as in claim 17, wherein the dental treatment composition comprises a sticky viscous gel, a less viscous gel, a highly viscous putty, or a substantially solid adhesive composition that is less adhesive prior to being moistened with saliva or water but that becomes more sticky and adhesive when moistened.

19. A pre-shaped, non-customized dental treatment device as in claim 17, wherein the dental treatment composition comprises at least one active agent selected from the group consisting of dental bleaching agents, dental desensitizing agents, antimicrobial agents, and anticariogenic agents.

20. A dental tray device kit comprising:
 a first dental tray device configured for placement over at least a portion of a person's lower dental arch comprising:
  a generally horseshoe-shaped moisture resistant barrier layer configured to substantially correspond to the curvature of a person's lower dental arch and having sufficient flexibility without heating in boiling water so as to readily conform to a plurality of differently sized lower dental arches corresponding to different people without customization;
  the barrier layer having an anterior region that at least partially covers anterior teeth surfaces when worn and a posterior region that at least partially covers posterior teeth surfaces when worn;
  the barrier layer being substantially devoid of structures corresponding to the size and shape of a person's unique dentition so that the barrier layer is designed to comfortably fit over a plurality of differently-sized and/or shaped teeth of lower dental arches corresponding to different people; and the barrier layer having a labial-buccal wall in the posterior and anterior regions, a lingual wall in the anterior region but not the posterior region, and a bottom wall interposed between the labial-buccal wall and the lingual wall in the anterior region and extending laterally relative to the labial-buccal wall in the posterior region, wherein a width of the bottom wall in the posterior region is equal to or less than a width of the bottom wall in the anterior region; and a second dental tray device configured for placement over at least a portion of a person's upper dental arch comprising:

a generally horseshoe-shaped moisture resistant barrier layer configured to substantially correspond to the curvature of a person's upper dental arch and having sufficient flexibility without heating in boiling water so as to readily conform to a plurality of differently sized upper dental arches corresponding to different people without customization;

the barrier layer having an anterior region that at least partially covers anterior teeth surfaces when worn and a posterior region that at least partially covers posterior teeth surfaces when worn;

the barrier layer being substantially devoid of structures corresponding to the size and shape of a person's unique dentition so that the barrier layer is designed to comfortably fit over a plurality of differently-sized and/or shaped teeth of upper dental arches corresponding to different people; and the barrier layer having a labial-buccal wall in the posterior and anterior regions, a lingual wall in the anterior region but not the posterior region, and a bottom wall interposed between the labial-buccal wall and the lingual wall in the anterior region and extending laterally relative to the labial-buccal wall in the posterior region, wherein a width of the bottom wall in the posterior region is equal to or less than a width of the bottom wall in the anterior region.

\* \* \* \* \*

UNITED STATES PATENT AND TRADEMARK OFFICE
CERTIFICATE OF CORRECTION

PATENT NO. : 8,721,332 B2
APPLICATION NO. : 13/742080
DATED : May 13, 2014
INVENTOR(S) : Fischer et al.

Page 1 of 1

It is certified that error appears in the above-identified patent and that said Letters Patent is hereby corrected as shown below:

In the Specification

Column 2
Line 45, change "configured for placed" to -- configured for placement --

Column 4
Line 9, change "person' lower dental arch" to -- person's lower dental arch --
Line 44, change "persons lower dental arch" to -- person's lower dental arch --

Column 6
Line 34, change "refers to number average" to -- refers to the number of average --

Column 8
Line 45, change "so as to effect treatment" to -- so as to affect treatment --

Column 25
Line 59, change "had it greatest width" to -- had its greatest width --

Column 26
Line 10, change "had it greatest width" to -- had its greatest width --

Signed and Sealed this
Twenty-eighth Day of October, 2014

Michelle K. Lee
*Deputy Director of the United States Patent and Trademark Office*